(12) United States Patent
Kilpatrick et al.

(10) Patent No.: US 7,794,951 B2
(45) Date of Patent: Sep. 14, 2010

(54) SREBP2GC TRANSCRIPTION FACTORS AND USES THEREOF

(75) Inventors: Daniel Kilpatrick, Shrewsbury, MA (US); Hang Wang, Worcester, MA (US)

(73) Assignee: University of Massachusetts Medical School, Boston, MA (US)

( * ) Notice: Subject to any disclaimer, the term of this patent is extended or adjusted under 35 U.S.C. 154(b) by 655 days.

(21) Appl. No.: 11/253,012

(22) Filed: Oct. 18, 2005

(65) Prior Publication Data

US 2007/0089179 A1 Apr. 19, 2007

(51) Int. Cl.
- G01N 33/53 (2006.01)
- G01N 33/567 (2006.01)
- C12Q 1/00 (2006.01)

(52) U.S. Cl. .................. 435/7.1; 435/4; 435/7.21; 435/7.8

(58) Field of Classification Search .............. 435/4, 435/6, 7.1, 7.21, 7.8

See application file for complete search history.

(56) References Cited

U.S. PATENT DOCUMENTS

| | | | |
|---|---|---|---|
| 4,816,567 A | 3/1989 | Cabilly et al. |
| 4,873,191 A | 10/1989 | Wagner et al. |
| 4,981,785 A | 1/1991 | Nayak |
| 5,034,506 A | 7/1991 | Summerton et al. |
| 5,223,409 A | 6/1993 | Ladner et al. |
| 5,358,691 A | 10/1994 | Clark et al. |
| 5,489,677 A | 2/1996 | Sanghvi et al. |
| 5,539,082 A | 7/1996 | Nielsen et al. |
| 5,585,089 A | 12/1996 | Queen et al. |
| 5,599,677 A | 2/1997 | Dowell et al. |
| 5,602,240 A | 2/1997 | De Mesmaeker et al. |
| 5,614,396 A | 3/1997 | Bradley et al. |
| 5,618,682 A | 4/1997 | Scheirer |
| 5,672,480 A | 9/1997 | Dowell et al. |
| 5,674,713 A | 10/1997 | Mcelroy et al. |
| 5,705,188 A | 1/1998 | Junichi et al. |
| 5,714,331 A | 2/1998 | Buchardt et al. |
| 5,719,262 A | 2/1998 | Buchardt et al. |
| 5,824,544 A | 10/1998 | Armentano et al. |
| 5,830,730 A | 11/1998 | German et al. |
| 5,871,907 A | 2/1999 | Winter et al. |
| 5,872,154 A | 2/1999 | Wilson |
| 5,885,530 A | 3/1999 | Babson et al. |
| 5,885,808 A | 3/1999 | Spooner et al. |
| 5,976,796 A | 11/1999 | Szalay et al. |
| 5,981,225 A | 11/1999 | Kochanek et al. |
| 5,994,106 A | 11/1999 | Kovesdi et al. |
| 5,994,128 A | 11/1999 | Fallaux et al. |
| 5,994,132 A | 11/1999 | Chamberlain et al. |
| 6,001,557 A | 12/1999 | Wilson et al. |
| 6,019,978 A | 2/2000 | Ertl et al. |
| 6,033,908 A | 3/2000 | Bout et al. |
| 6,054,297 A | 4/2000 | Carter et al. |
| 6,074,859 A | 6/2000 | Hirokawa et al. |
| 6,080,912 A | 6/2000 | Bremel et al. |
| 6,159,750 A | 12/2000 | Edmonds |
| 6,180,370 B1 | 1/2001 | Queen et al. |
| 6,180,377 B1 | 1/2001 | Morgan et al. |
| 6,506,559 B1 | 1/2003 | Fire et al. |
| 7,202,023 B2 | 4/2007 | Murphy |
| 7,244,557 B2 | 7/2007 | Nunez et al. |
| 7,306,938 B2 | 12/2007 | Murphy et al. |
| 7,364,842 B2 | 4/2008 | Chao et al. |
| 7,396,524 B2 | 7/2008 | Yan |

FOREIGN PATENT DOCUMENTS

| | | |
|---|---|---|
| WO | WO 90/08832 | 8/1990 |
| WO | WO 97/30731 | 8/1997 |
| WO | WO 99/02685 | 1/1999 |
| WO | WO 00/09675 | 2/2000 |
| WO | WO 00/12738 | 3/2000 |
| WO | WO 01/98537 | 12/2001 |

OTHER PUBLICATIONS

Baliga NS, 2001, Biol. Proced. Online, vol. 3, No. 1 pp. 64-69.*
Hecht (1998) "Molecular Mechanisms of Male Germ Cell Differentiation," Bioessays 20:555-561.
Eddy (1998) "Regulation of Gene Expression During Spermatogenesis," Semin Cell Dev Biol 9:451-57.
Eddy and O'Brien (1998) "Gene Expression During Mammalian Meiosis" Curr Top Dev Biol 37:141-200.
Cunliffe et al. (1990) "Genomic Analysis of a Mouse Zinc Finger Gene, Zfp-35, that is Up-Regulated During Spermatogenesis" Genomics 8:331-39.
Bellefroid et al. (1998) "Kzfl—A Novel KRAB Zinc Finger Protein Encoding Gene Expressed During Rat Spermatogenesis" Biochim Biophys Acta 1398:321-29.
Noce et al. (1993) "A Novel Murine Zinc Finger Gene Mapped Within the tw18 Deletion Region Expresses in Germ Cells and Embryonic Nervous System" Dev Biol 155:409-22.
Lee et al. (1996) "Molecular Cloning and Characterization of a Mouse Nuclear Orphan Receptor Expressed in Embryos and Testes" Mol Reprod Dev 44:305-14.
Blendy et al. (1996) "Severe Impairment of Spermatogenesis in Mice Lacking the CREM Gene" Nature 380:162-65.
Nantel et al. (1996) "Spermiogenesis Deficiency and Germ-Cell Apoptosis in CREM-Mutant Mice" Nature 380:159-62.
Fimia et al. (1999) "CBP-Independent Activation of CREM and CREB by the LIM-Only Protein ACT" Nature 398:165-9.

(Continued)

*Primary Examiner*—Peter Paras, Jr.
*Assistant Examiner*—David Montanari
(74) *Attorney, Agent, or Firm*—Medlen & Carroll, LLP

(57) ABSTRACT

The present invention relates to methods and compositions for modulating fertility. In particular the present invention provides cell lines and transgenic animals for use in identifying modulators of SREBP2gc transcription factors. The present invention further provides therapeutic agents that modulate SREBP2gc signaling for use as fertility modulators.

18 Claims, 6 Drawing Sheets

OTHER PUBLICATIONS

Han et al. (2001) "TFIIAα/β-Like Factor Is Encoded by a Germ Cell-Specific Gene Whose Expression Is Up-Regulated with Other General Transcription Factors During Spermatogenesis in the Mouse" Biol Reprod 64:507-17.

Martianov et al. (2001) "Late Arrest of Spermiogenesis and Germ Cell Apoptosis in Mice Lacking the TBP-Like *TLF/TRF2* Gene" Mol Cell Biol 7:509-15.

Delmas et al. (1993) "Induction of CREM Activator Proteins in Spermatids: Down-Stream Targets and Implications for Haploid Germ Cell Differentiation" Mol Endocrinol 7:1502-14.

Wang et al. (2002) "Expression of a Novel, Sterol-Insensitive Form of Sterol Regulatory Element Binding Protein 2 (SREBP2) in Male Germ Cells Suggests Important Cell- and Stage-Specific Functions for SREBP Targets during Spermatogenesis" Mol Cell Biol 22:8478-90.

Horton et al. (2002) "SREBPs: Activators of the Complete Program of Cholesterol and Fatty Acid Synthesis in the Liver" J Clin Invest 109:1125-31.

Edwards et al. (2000) "Regulation of Gene Expression by SREBP and SCAP" Biochim Biophys Acta 1529:103-13.

Foulkes et al. (1992) "Developmental Switch of CREM Function During Spermatogenesis: From Antagonist to Activator" Nature 355:80-84.

Shimano (2001) "Sterol Regulatory Element-Binding Proteins (SREBPs): Transcriptional Regulators of Lipid Synthetic Genes" Prog Lipid Res 40:439-52.

Worgall et al. (2004) "Sterol and Fatty Acid Regulatory Pathways in *Giardia Lamblia*-Derived Promoter: Evidence for SREBP as an Ancient Transcription Factor" J Lipid Res 45:981-88.

Schulten et al. (1999) "Yeast One-Hybrid Assay Identifies YY1 as a Binding Factor for a Proacrosin Promoter Element" Biochem Biophys Res Commun 257:871-73.

Kistler et al. (1994) "Identification of a Functional Cyclic Adenosine 3',5'-Monophosphate Response Element in the 5'-Flanking Region of the Gene for Transition Protein 1 (TP1), a Basic Chromosomal Protein of Mammalian Spermatids" Biol Reprod 51:1322-29.

Yiu and Hecht (1997) "Novel Testis-Specific Protein-DNA Interactions Activate Transcription of the Mouse Protamine 2 Gene During Spermatogenesis" J Biol Chem 272:26926-33.

Zhang et al. (1999) "Multiple Elements Influence Transcriptional Regulation from the Human Testis-Specific *PGK2* Promoter in Transgenic Mice" Biol Reprod 60:1329-37.

Schulten et al. (2001) "Assessment of Promoter Elements of the Germ Cell-Specific Proacrosin Gene" J Cell Biochem 83:155-62.

Nikolajczyk et al. (1995) "A Mouse Homologue of the Xenopus Germ Cell-Specific Ribonucleic Acid/Deoxyribonucleic Acid-Binding Proteins p54/p56 Interacts with the Protamine 2 Promoter" Biol Reprod 52:524-30.

Vanden Heuvel et al. (1996) "A Unique Variant of a Homeobox Gene Related to *Drosophilia cut* Is Expressed in Mouse Testis" Biol Reprod 55:731-39.

Sogawa et al. (1993) "cDNA Cloning and Transcriptional Properties of a Novel GC Box-Binding Protein, BTEB2" Nucleic Acids Res 21:1527-32.

Stelzer and Don (2002) "*Atcel*: A Novel Mouse Cyclic Adenosine 3',5'-Monophosphate-Responsive Element-Binding Protein-Like Gene Exclusively Expressed in Postmeiotic Spermatids" Endocrinology 143:1578-88.

Persengiev et al. (1996) "Transcription Factor Sp1 Is Expressed by Three Different Developmentally Regulated Messenger Ribonucleic Acids in Mouse Spermatogenic Cells*" Endocrinology 137:638-46.

Singh and Chakravarty (2003) "Antispermatogenic and Antifertility Effects of 20,25-Diazacholesterol Dihydrochloride in Mice" Reprod Toxicol 17:37-44.

Wechsler et al. (2003) "Generation of Viable Cholesterol-Free Mice" Science 302:2087.

Teruya et al. (1991) "Testis-Specific Transcripts of Rat Farnesyl Pyrophosphate Synthetase are Developmentally Regulated and Localized to Haploid Germ Cells" Biol Reprod 44:663-71.

Tacer et al. (2002) "Tissue-Specific Transcriptional Regulation of the Cholesterol Biosynthetic Pathway Leads to Accumulation of Testis Meiosis-Activating Sterol (T-MAS)" J Lipid Res 43:82-89.

Potter et al. (1981) "Elevated Cholesterol and Dolichol Synthesis in Mouse Pachytene Spermatocytes" J Biol Chem 256:7150-54.

deWet et al. (1987) "Fiefly Luciferase Gene: Structure and Expression in Mammalian Cells" Mol Cell Biol 7:725-37.

Graham and van der Eb (1973) "A New Technique for the Assay of Infectivity of Human Adenovirus 5 DNA" Virol 52:456-67.

Brinster et al. (1985) "Factors Affecting the Efficiency of Introducing Foreign DNA into Mice by Micoinjecting Eggs" Proc. Natl. Acad. Sci. 82:4438-42.

Janenich (1976) "Germ Line Integration and Mendelian Transmission of the Exogenous Moloney Leukemia Virus" Proc. Natl. Acad. Sci. 73:1260-64.

Jahner et al. (1985) "Insertion of the Bacterial *gpt* Gene into the Germ Line of Mice by Retroviral Infection" Proc. Natl. Acad Sci. 82:6927-31.

Jahner et al. (1982) "De Novo Methylation and Expression of retroviral Genomes During Mouse Embryogenesis" Nature 298:623-28.

Haskell and Bowen (1995) "Efficient Production of Transgenic Cattle by Retroviral Infection of Early Embryos" Mol Reprod Dev 40:386-90.

Evans et al. (1981) "Establishment in Culture of Pluripotential Cells from Mouse Embryos" Nature 292:154-156.

Bradley et al. (1984) "Formation of Germ-Line Chimaeras from Embryo-Derived Teratocarcinoma Cell Lines" Nature 309:255-56.

Gossler et al. (1986) "Transgenesis by Means of Blastocyst-Derived Embryonic Stem Cell Lines" Proc. Natl. Acad. Sci. 83:9065-69.

Robertson et al. (1986) "Clues about RNA Enzymes" Nature 322:16-17.

Jaenisch (1988) "Transgenic Animals" Science 240:1468-1474.

Zuckermann et al. (1994) "Discovery of Nanomolar Ligands for 7-Transmembrane G-Protein-Coupled Receptors From a Diverse N-(substituted) Glycine Peptoid Library" J Med Chem 37:2678-85.

Lam (1997) "Application of Combinatorial Library Methods in Cancer research and Drug Discovery" Anticancer Drug Des 12:145-67.

DeWitt et al. (1993) "Diversomers": An Approach to Nonpeptide, Nonoligomeric Chemical Diversity Proc. Natl. Acad. Sci. 90:6909-13.

Erb et al. (1994) Recursive Deconvolution of Combinatorial Chemical Librari Proc. Natl. Acad. Sci. 91:11422-26.

Cho et al. (1993) "An Unnatural Biopolymer" Science 261:1303-05.

Carrell et al. (1994) "A Novel Procedure for the Synthesis of Libraries Containing Small Organic Molecules" Angew. Chem. Int. Ed. Engl. 33:2059-61.

Carell et al. (1994) "A Solution-Phase Screening Procedure for the Isolation of Active Compounds from a Library of Molecules" Angew. Chem. Int. Ed. Engl. 33:2061-64.

Gallop et al. (1994) "Applications of Combinatorial Technologies to Drug Discovery. 1. Background and Peptide Combinatorial Libraries" J Med Chem 37:1233-1251.

Houghten (1992) "The Use of Synthetic Peptide Combinatorial Libraries for the Identification of Bioactive Peptides" Biotechniques 13:412-21.

Lam (1991) "A New Type of Synthetic Peptide Library for Identifying Ligand-Binding Activity" Nature 354:82-84.

Fodor (1993) "Multiplexed biochemical assays with biological ships," Nature 364:555-56.

Cull et al. (1992) "Screening for Receptor Ligands Using Large Libraries of Peptides Linked to the C Terminus of the *lac* Repressor" Proc. Natl. Acad. Sci. 89:1865-69.

Scott and Smith (1990) "Searching for Peptide Ligands with an Epitope Library" Science 249:386-90.

Devlin (1990) "Random Peptide Libraries: A Source of Specific Protein Binding Molecules" Science 249:404-06.

Cwirla et al. (1990) Peptides on Phage: A Vast Library of Peptides for Identifying Ligands Proc. Natl. Acad. Sci. 87:6378-82.

Felici (1991) "Selection of Antibody Ligands from a Large Library of Oligopeptides Expressed on a Multivalent Exposition Vector" J. Mol. Biol 222:301-310.

Tuschl and Borkhardt (2002) "Small Interfering RNAs: A Revolutionary Tool for the Analysis of Gene Function and Gene Therapy" Molecular Intervent 2:158-67.

Caplen et al. (2001) "Specific Inhibition of Gene Expression by Small Double-Stranded RNAs in Invertebrate and Vertebrate Systems" Proc. Natl. Acad Sci. 98:9742-7.

Elbashir et al. (2001) "Duplexes of 21-Nucleotide RNAs Mediate RNA Interference in Cultured Mammalian Cells" Nature 411:494-8.

Elbashir et al. (2001) "RNA Interference is Mediated by 21- and 22-Nucleotide RNAs" Genes Dev 15:188-200.

Elbashir et al. (2001) "Functional Anatomy of siRNAs for Mediating Efficient RNAi in *Drosophila melanogaster* Embryo Lysate" EMBO J. 20:6877-88.

Brummelkamp et al. (2002) "A System for Stable Expression of Short Interfering RNAs in Mammalian Cells" Science 296:550-3.

Holen et al. (2002) "Positional Effects of Short Interfering RNAs Targeting the Human Coagulation Trigger Tissue Factor" Nucleic Acids Res 30:1757-66.

Nielsen et al. (1991) "Sequence-Selective Recognition of DNA by Strand Displacement with a Thymine-Substituted Polyamide" Science 254:1497-1500.

Martin et al. (1995) "Ein neuer Zugang zu 2'-O-Alkylribonucleosiden und Eigenschaften deren Oligonucleotide" Helv Chim Acta 78:486-504.

Annicotte et al. (2001) "An E-Box in pGL3 Reporter Vectors Precludes Their Use for the Study of Sterol Regulatory Element-Binding Proteins" Biotechniques 31:993-4, 996.

Liu et al. (1997) "Novel Repeat Elements Direct Rat Proenkephalin Transcription During Spermatogenesis" J Biol Chem 272:5056-62.

Swinnen et al. (1998) "Identification of Diazepam-Binding Inhibitor/Acyl-CoA-Binding Protein as a Sterol Regulatory Element-Binding Protein-Responsive Gene" J Biol Chem 273:19938-44.

Tascou et al. (2000) "Immortalization of Murine Male Germ Cells at a Discrete Stage of Differentiation by a Novel Directed Promoter-Based Selection Strategy" Biol Reprod 63:1555-61.

Guan et al. (1998) "Differential Transcriptional Regulation of the Human Squalene Synthase Gene by Sterol Regulatory Element-binding Proteins (SREBP) 1a and 2 and Involvement of 5' DNA Sequence Elements in the Regulation" J Biol Chem 273:12526-35.

Stromstedt et al (1998) "Elevated Expression of Lanosterol 14α-Demethylase (CYP51) and the Synthesis of Oocyte Meiosis-Activating Sterols in Postmeiotic Germ Cells of Male Rats" Endocrinology 139:2314-21.

Adham et al. (1997) "Spermatozoa Lacking Acrosin Protein Show Delayed Fertilization," Mol Reprod Dev 46:370-76.

Nayernia et al. (2003) "Synergistic effects of germ cell expressed genes on male fertility in mice," Cytogenet Genome Res 103:314-20.

Yamagata et al. (1998) "Acrosin Accelerates the Dispersal of Sperm Acrosomal Proteins during Acrosome Reaction," J Biol Chem 273:10470-74.

Kashiwabara et al. (1990) "Acrosin Biosynthesis in Meiotic and Postmeiotic Spermatogenic Cells," Biochem Biophys Res Common 173:240-45.

Hofmann et al. (1992) "Immortalization of Germ Cells and Somatic Testicular Cells Using the SV40 Large T Antigen" Exper Cell Res 201:417-35.

Rozman et al. (1999) "Cyclic Adenosine 3', 5'-Monophosphate(cAMP)/cAMP-Responsive Element Modulator (CREM)-Dependent Regulation of Cholesterogenic Lanosterol 14α-Demethylase (CYP51) in Spermatids" Mol Endocrinol 13:1951-62.

Kremling et al. (1991) "Mouse Proacrosin Gene: Nucleotide Sequence, Diploid Expression, and Chromosomal Localization," Genomics 11:828-34.

Ikeda et al. (2001) "Transcriptional Regulation of the Murine Acetyl-CoA Synthetase 1 Gene through Multiple Clustered Binding Sites for Sterol Regulatory Element-binding Proteins and a Single Neighboring Site for Sp1" J Biol Chem 276:34259-69.

Nayernia et al. (1994) "Functional and Molecular Characterization of the Transcriptional Regulatory of the Proacrosin Gene" J Biol Chem 269:32181-86.

Palmiter and Brinster (1986) "Germ-line transformation of mice" Annu Rev Genet 20:465-99.

Nayernia et al. (1994) "Diploid Expression and Translational Regulation of Rat Acrosin Gene" Biochem Biophys Res Commun 202:88-93.

Wang et al. (2004) "Novel Role for a Sterol Response Element Binding Protein in Directing Spermatogenic Cell-Specific Gene Expression," Mol. and Cell. Biol. 24:10681-10688.

Suen et al. "A potential transcriptional adaptor(s) may be required in thyroid hormone-stimulated gene transcription in vitro," Endrocrinology (1995) 136(6):2776-83.

Tong et al. "Ligand modulates the interaction of thyroid hormone receptor beta with the basal transcription machinery," J. Biol. Chem. (1995) 270(18):10601-11.

Dilworth et al. "In vitro transcription system delineates the distinct roles of the coactivators pCAF and p300 during MyoD/E47-dependent transactivation," Proc Natl Acad Sci U S A. (2004) Aug. 10;101(32):11593-8.

Choudhry et al. "In vitro regulation of reporter gene transcription by the androgen receptor AF1 domain," Biochem Soc Trans. Dec. 2004;32(Pt 6):1103-6.

Wang et al., "Expression of a Sterol-Insensitive Form of SREBP2 in Male Germ Cells Suggests Important Cell- and Stage-Specific Functions for SREBP Targets During Spermatogenesis," Molec. Cell. Biol. Dec. 2002; 22(24): 8478-8490.

Wang et al., "*A Role for Nuclear Factor I in the Intrinsic Control of Cerebellar Granule Neuron Gene Expression*," J. Biol. Chem. Dec. 2004; 279(51):53491-7.

Brown et al., "Suppression of oncogene-induced transformation by a deletion mutant of c-jun," Oncogene Apr. 1993; 8(4):877-86. PMID: 8455942.

* cited by examiner

Figure 6

SREpa1  M  G<u>CACTTCAG</u>CACAG<u>ATCAG</u> (-123,-141)    SREpa2  M  *ATGGGTTGG*TT<u>GCACATGAGT</u>ACCTTC<u>ACCACCCTGAGGTCAG</u> (-168, -209)

R  TG<u>GCACCTCAGCG</u> (-133, -145)    R  CTCATGAGT*ACCTC*A*CCAC*CCT<u>GAGGCGG</u> (-170, -198)

SREpa3  M  GG*CTGGCCAA* (-240, -249)    SREpa4  M  *ACCTTTCCATACTAT* (-782,-796)    SREpa5  M  *CTGGATGGGTAGGA* (-844,-857)

R  GG*CTCGCCAA* (-239, -248)    R  *GCCTTTCCATGCTA*TAA<u>GAGG</u> (-763, -784)    R  GT*CTCGATGGGTAGGA* (-822, -837)

HUMAN SREs  *TTGCAGGCCAGGC* (-13, -24)  *ACCTGGCCTGACT* (-97, -109)  GG<u>GTGATGTGGGG</u> (-262, -274)  GT<u>CTGCAGTGGAC</u> (-333, -345)

Table 1. Sequences of putative SREs in the mouse (M), rat (R) and human proacrosin promoters. SRE half-sites are under- or overlined, and NNCNNNCNAN motifs are italicized. Numbers in parentheses indicate the positions of the first and last bases within respective proacrosin promoter nucleotide sequences relative to the translational start site (+1).

SREBP2GC TRANSCRIPTION FACTORS AND USES THEREOF

This application was supported in part by Public Service Grants R01 DK36468 and DK32520, awarded by the national institutes of health. The government may have certain rights in the invention.

FIELD OF THE INVENTION

The present invention relates to methods and compositions for modulating fertility. In particular the present invention provides cell lines and transgenic animals for use in identifying modulators of SREBP2gc transcription factors. The present invention further provides therapeutic agents that modulate SREBP2gc signaling for use as fertility modulators.

BACKGROUND OF THE INVENTION

Birth control methods include barrier methods (e.g., condoms, diaphragm, etc.), intrauterine devices (IUDs), hormonal methods, surgical sterilization, and natural family planning.

Hormonal methods, which include pills, shots, rings, and patches, are very reliable means of birth control. Hormonal methods use two basic formulas: a combination of estrogen and progestin or progestin only. Pill based methods have the disadvantage of requiring daily dosing at the same time every day. In addition, each type of hormonal birth control has the potential of side effects such as nausea, irregular periods, and headaches.

Intrauterine devices are also very effective but have the potential to cause side effects such as longer and heavier periods and increased cramping. All types of IUDs may be uncomfortable when inserted, especially in women who have not had a baby.

Barrier methods, such as condoms, diaphragms, cervical caps, Lea's shield, sponges, and spermicides are less reliable than hormonal or IUD methods and require application before each use. Depending on the product, proper use can require some training and practice.

Fertility awareness (natural family planning), such as the calendar method can be successful if partners are very careful about figuring fertile times of the month and not having sex or using birth control methods during these times. This method is not appropriate for sexually active teens or women who are not able to predict when they ovulate.

Sterilization (e.g., tubal ligation or vasectomy) is one of the most reliable methods of birth control. However, sterilization is permanent, with the rate of successful reversal very low. Sterilization, in particular tubal ligation, is a surgical procedure that requires general anesthesia, which carries its own risks.

What are needed in the art are additional safe, reliable methods of birth control.

SUMMARY OF THE INVENTION

The present invention relates to methods and compositions for modulating fertility. In particular the present invention provides cell lines and transgenic animals for use in identifying modulators of SREBP2gc transcription factors. The present invention further provides therapeutic agents that modulate SREBP2gc signaling for use as fertility modulators.

Accordingly, in some embodiments, the present invention provides methods and compositions for use in identifying modulators of SREBP2gc activity. In some embodiments, the activation of proacrosin promoter based gene expression is used as a screening assay to identify modulators of SREBP2gc transcription factor activity. The present invention further provides therapeutic agents (e.g., identified using the drug screening methods of the present invention) for use in modulating fertility (e.g., as contraceptive agents).

For example, in some embodiments, the present invention provides a method of screening compounds, comprising: providing a nucleic acid comprising a proacrosin promoter; a SREBP2gc polypeptide; and one or more test compounds; and contacting the proacrosin promoter and the SREBP2gc polypeptide with the test compound; and detecting a change in expression from the proacrosin promoter in the presence of the test compound relative to the absence of the test compound. In preferred embodiments, the test compound decreases expression from the proacrosin promoter. In certain embodiments, the proacrosin promoter is operably linked to a reporter gene. In some embodiments, the method further comprises the step of selecting a compound with the desired effect and administering the compound to a subject. In some embodiments, the SREBP2gc polypeptide is provided as a nucleic acid encoding the SREBP2gc polypeptide. In some embodiments, the proacrosin promoter has the nucleic acid sequence of SEQ ID NO: 15. In some embodiments, the proacrosin promoter comprises one or more sterol response elements (e.g., those described by SEQ ID NOs: 1-14). In some embodiments, the sterol response elements are mutant sterol response elements (e.g., non-functional). In some embodiments, the proacrosin promoter, the SREBP2gc polypeptide and the test compound are in a cell. In some preferred embodiments, the cell is a spermatocyte cell line (e.g., a GC-4 spc cell line). In some embodiments, the cell is in a non-human animal (e.g., a mouse).

The present invention further provides a therapeutic agent identified using the drug screening method (e.g., a therapeutic agent that inhibits SREBP2gc activity and decreases sperm count in a mammal).

The present invention also provides a transgenic animal comprising an exogenous proacrosin promoter. In some preferred embodiments, the proacrosin promoter is operably linked to a reporter gene (e.g., a luciferase gene). In some embodiments, the proacrosin promoter comprises one or more sterol response elements (e.g., as described by SEQ ID NOS: 1-14). In some embodiments, the sterol response elements are mutant sterol response elements (e.g., non-functional elements). In some embodiments, the transgenic animal is a mouse.

The present invention further provides a method of screening test compounds comprising administering a test compound (e.g., one identified using the methods of the present invention) to a transgenic animal comprising an exogenous proacrosin promoter. In some embodiments, the method further comprises identifying the effect of the test compound on expression levels from the proacrosin promoter. In some embodiments, the method further comprises assaying the level of toxicity of said test compound.

DESCRIPTION OF THE FIGURES

FIG. 1A shows RT-PCR analysis of SREBP2gc mRNA. FIG. 1B shows Northern analysis using total RNA from GC-4spc cells (15 μg); 21-day old mouse testis (MT, 20 μg); purified mouse pachytene spermatocytes (20 μg). FIG. 1C shows EMSA of SREBPs in GC-4spc cells.

FIG. 2A shows luciferase activity of GC-4spc and 3T3L1 cells transfected with human SQS promoter constructs containing either wild-type or mutated (MSQS) SRE sites. FIG. 2B shows luciferase activity after co-transfection of GC-4spc cells with wild-type or mutant SQS promoter plasmids together with either an expression vector for SREBP2gc (BP2GC) or the empty parent plasmid (CMV7). FIG. 2C shows luciferase activity after co-transfection of the rat proacrosin promoter together with SREBP2gc or pCMV7 expression plasmids in different cell lines. FIG. 2D shows luciferase activity from cell lines co-transfected with either SQS (NIH-3T3, GC-1spg) or CYP51 (JEG3, GC-4spc) promoter plasmids and expression vectors.

FIG. 3A shows the organization of SREs within the rat, mouse and human proacrosin promoters. FIGS. 3B, C, and D show competitive EMSAs using adult mouse germ cell nuclear extracts (2 μg) and rat proacrosin SRE sites. FIG. 3E shows the results of Southwestern analysis using SREpa2.

FIG. 4A shows activities of different proacrosin promoter plasmids in GC-4spc cells co-transfected with either empty pCMV7 (empty bars) or SREBP2gc (filled bars) expression vectors. FIG. 4B shows luciferase activities for wildtype and SREpa2-5mut rat proacrosin-luciferase constructs in testicular extracts from male transgenic mice.

FIG. 6 shows a table of sequences of putative SREs in mouse (M), rat (R), and human. SREs are SREpa1 (M) (SEQ ID NO:1); SREpa1 (R) (SEQ ID NO:2); SREpa2 (M) (SEQ ID NO:3); SREpa2 (R) (SEQ ID NO:4); SREpa3 (M) (SEQ ID NO:5); SREpa3 (R) (SEQ ID NO:6); SREpa4 (M) (SEQ ID NO:7); SREpa4 (R) (SEQ ID NO:8); SREpa5 (M) (SEQ ID NO:9); SREpa5 (R) (SEQ ID NO:10); SRE human 1 (SEQ ID NO:11); SRE human 2 (SEQ ID NO:12); SRE human 3 (SEQ ID NO:13); and SRE human 4 (SEQ ID NO:14).

GENERAL DESCRIPTION OF THE INVENTION

Figure 1:
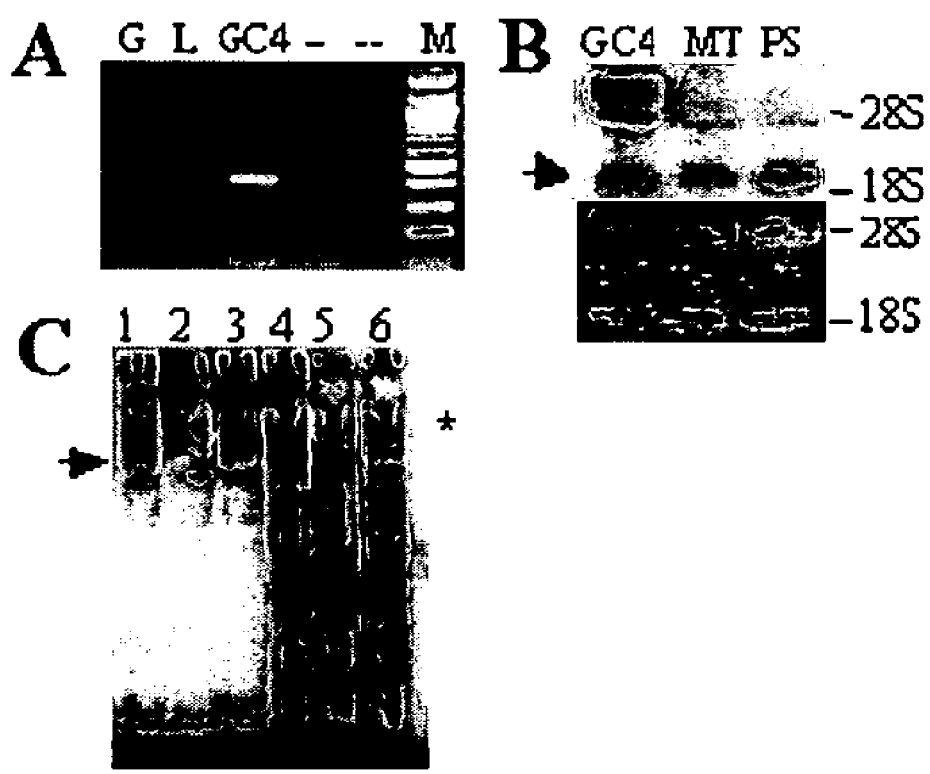
FIG. 1 shows that GC-4spc cells express SREBP2gc.

Sperm are highly differentiated cells that are uniquely adapted to their function as motile cells mediating fertilization. As such, they serve as an important model for exploring regulatory programs responsible for cellular differentiation (Hecht, (1998) Bioessays 20, 555-61). Spermatogenesis consists of a complex interplay between cell-specific gene transcription, RNA processing and translational regulation (Hecht et al., supra; Eddy, (1998) Semin Cell Dev Biol 9, 451-7). It occurs in a series of proliferative and differentiative stages, which can be subdivided into mitotic, meiotic and spermiogenic phases. Each phase is characterized by distinct cell types, namely, spermatogonia, spermatocytes and spermatids, respectively. The highly specialized nature of sperm is reflected in the large number of cell-specific transcripts and proteins they express (Eddy, (1998) Semin Cell Dev Biol 9, 451-7), many of which are associated with unique sperm structures such as the acrosome, sperm tail, and the highly compacted sperm chromosomal DNA. Unique proteins also are required to meet specialized requirements for energy metabolism, meiosis and the maturation of haploid cells, including cell-specific genes that compensate for X-chromosome inactivation (e.g., phosphoglycerate kinase 2 (pgk-2)) (Eddy and O'Brien, (1998) Curr Top Dev Biol 37, 141-200). These various gene products also must be expressed at the appropriate time to ensure normal development. Thus, sperm formation requires both the generation of a large number of cell-specific gene products as well as the coordination of this differentiation program in a stepwise, stage-appropriate manner.

Cell-specific transcription from alternative promoters or unique genes plays a predominant role in directing male germ cell differentiation (Eddy, (1998) Semin Cell Dev Biol 9, 451-7). Numerous spermatogenic cell-enriched transcription factors have been identified, many of which are selectively expressed during meiotic and/or early haploid stages (Cunliffe et al., (1990) Genomics 8, 331-9; Bellefroid et al., (1998) Biochim Biophys Acta 1398, 321-9; Noce et al., (1993) Dev Biol 155, 409-22; Lee et al., (1996) Mol Reprod Dev 44, 305-14). For example, the spermatogenic cell-specific factor, CREMτ, is an activator of several genes expressed in haploid spermatids and is required for completion of spermiogenesis (Blendy et al., (1996) Nature 380, 162-165; Nantel et al., (1996) Nature 380, 159-162). CREMτ also interacts with a germ cell-specific co-activator termed ACT (Fimia et al., (1999) Nature 398, 165-9), and several unique germ cell isoforms of basal transcription factors also have been identified (Han et al., (2001) Biol. Reprod 64, 507-17; Martianov et al., (2001) Mol Cell 7, 509-15). All this indicates that spermatogenic cells have evolved a highly specialized transcriptional program. However, functional identification of transcription factors responsible for controlling spermatogenic cell differentiation has been elusive. Prior to the present invention, CREMτ was the only spermatogenic cell-enriched transcription factor for which a physiological role and specific germ cell-specific target genes have been identified (Delmas et al., (1993) Mol. Endocrinol. 7, 1502-1514). Moreover, nothing is currently known about the cell-specific regulators of gene promoters expressed in spermatocytes.

SREBP2gc is 55 kilodalton (kDa), germ cell-enriched form of the basic helix-loop-helix leucine zipper (bHLHZip) transcription factor Sterol Response Element Binding Protein 2 (SREBP2) (Wang et al., (2002) Mol Cell Biol 22, 8478-90). Its expression is highly up-regulated during late meiosis and in early round spematids, suggesting stage-specific functions. In somatic cells, SREBP2 regulates genes involved mainly in cholesterol synthesis (Horton et al., (2002) J Clin Invest 109, 1125-31), and its transcriptional activity is highly dependent on the function of coregulatory factors such as CREB/CREM, NF-Y, Sp1, and the SREBP antagonist YY1 (Edwards et al., (2000) Biochim Biophys Acta 1529, 103-113). SREBPs are synthesized as membrane-bound precursor proteins that are proteolytically processed in the Golgi to generate a cytoplasmic, transcriptionally active mature SREBP. Sterols regulate this processing step as part of a homeostatic, feedback control mechanism by blocking the transport of SREBP precursor from the endoplasmic reticulum to the Golgi (Horton et al., supra). In contrast to this, translation of the alternatively spliced SREBP2gc mRNA generates a soluble, constitutively active transcription factor that consequently is insensitive to cholesterol feedback control (Wang et al., supra). Experiments conducted during the course of development of the present invention demonstrated that SREBP2gc regulates the transcription of a spermatogenic cell-specific gene, proacrosin, which is expressed in both spermatocytes and round spermatids. This factor likely regulates multiple gene targets as part of a global transcriptional program directing meiotic and post-meiotic stages of spermatogenic cell differentiation.

The importance of SREBPs in the homeostatic control of cholesterol and fatty acid synthesis in somatic cells is well established (Horton et al., supra). However, the finding of a constitutively active, sterol-insensitive form of SREBP2 that is expressed in a developmentally regulated manner in spermatogenic cells indicated a broader role for this factor not limited to lipid metabolism alone (Wang et al., supra). Experiments conducted during the course of development of the present invention implicate SREBP2gc in the stage-dependent expression of a spermatogenic cell specific gene, proacrosin, which is expressed in both spermatocytes and spermatids.

Together with CREMτ, SREBP2gc is only the second spermatogenic cell-enriched transcription factor shown to regulate a germ cell-specific promoter, and it is the first such factor that activates a gene expressed during male meiosis. Further, it is contemplated that SREBP2gc regulates multiple spermatogenic cell-specific genes, not proacrosin alone.

The present invention is not limited to a particular mechanism. Indeed, an understanding of the mechanism is not necessary to practice the present invention. Nonetheless, it is contemplated that, based on experiments conducted during the course of development of the present invention, a ubiquitous somatic factor (SREBP2) was adapted by spermatogenic cells to function in an entirely new manner as a trans-regulator of germ cell-specific genes. Precedent for this already exists in the form of CREMτ: analogous to SREBP2gc, it is a spermatogenic cell-specific variant of a generally expressed transcription factor family generated by alternative splicing. Both factors also possess unique properties that circumvent regulatory mechanisms operating in somatic cells and are critical for their function as spermatogenic cell trans-regulators. In the case of CREMτ, alternative splicing converts the CREM repressor into a germ cell-specific activator of CREs (Foulkes et al., (1992) Nature 355, 80-4). Further, phosphorylation mechanisms normally required for interactions with the CREB co-activator CBP do not apparently operate in spermatids. Instead, CREMτ interacts with the phosphorylation-independent co-activator ACT, which is expressed only in haploid spermatogenic cells along with CREMτ (Fimia et al., (1999) Nature 398, 165-9). This alternative pathway apparently evolved to provide for both stage- and cell-specific activation of CRE-dependent promoters in germ cells. Similarly, alternative splicing in spermatogenic cells generates an SREBP2 isoform that bypasses sterol-dependent inhibitory mechanisms, permitting stage-dependent up-regulation of a constitutively active factor and its target promoters in late spermatocytes and early spermatids.

Figure 5:
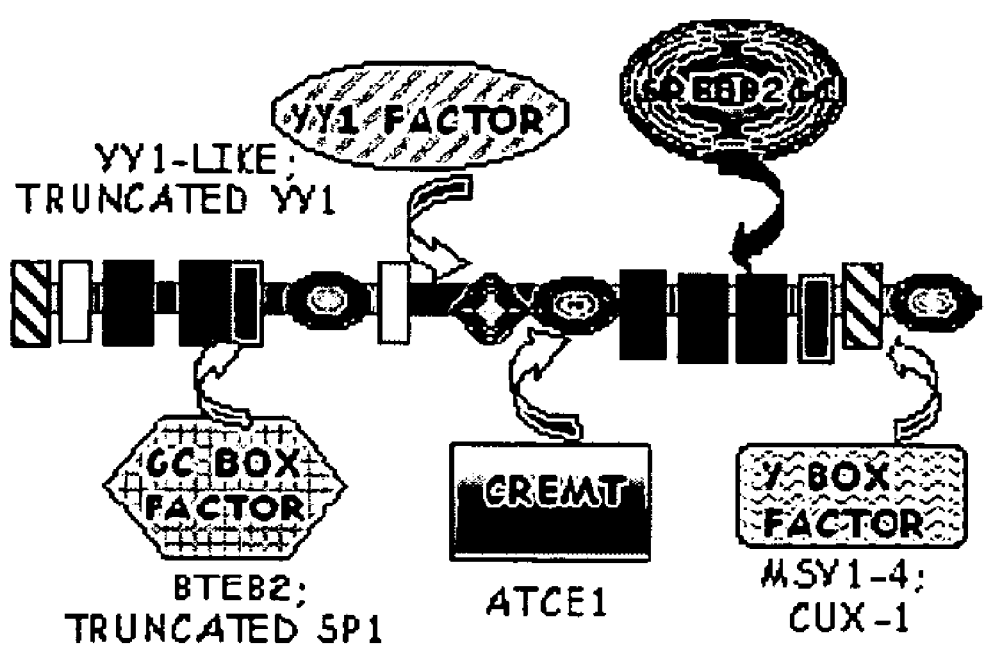
FIG. 5 shows that male germ cell-enriched isoforms of ubiquitous transcription factors function as co-regulators of spermatogenesis-specific genes.

SRE- and CRE-binding proteins act together to regulate numerous promoters in somatic cells (Shimano, (2001) Prog Lipid Res 40, 439-52). The present invention is not limited to a particular mechanism. Indeed, an understanding of the mechanism is not necessary to practice the present invention. Nonetheless, it is contemplated that SREBP2gc and CREMτ coordinately regulate common spermatogenic cell-specific promoters in spermatids. This may reflect a form of co-evolution of functionally related transcription factors, in which interacting partners take on cell-specific functions in parallel. It is further contemplated that these two proteins are members of a larger group of factors, including Y/CAAT- and GC-box binding factors as well as YY1-like proteins, specifically arising from more generally expressed trans-regulator families to control gene expression in the male germ line (FIG. 5). Such adaptation may be an efficient means for generating germ cell-specific transcription factors since it utilizes generally expressed, and perhaps ancient (Worgall et al., (2004) J Lipid Res.), trans-factors as well as response elements commonly found in RNA polymerase II promoters. Many germ cell-specific promoters expressed in late spermatocytes and/or round spermatids contain CRE, YY1, Y- and GC-box elements (Schulten et al., (1999) Biochem Biophys Res Commun 257, 871-3; Kistler et al., (1994) Biol. Reprod. 51, 1322-1329; Yiu and Hecht, (1997) J Biol Chem 272, 26926-33; Zhang et al., (1999) Biol Reprod 60, 1329-37), and unique, spermatogenic cell- or testis-enriched nuclear factors that bind these sites have been previously identified (Schulten et al., (2001) J Cell Biochem 83, 155-62; Nikolajczyk et al., (1995) Biol Reprod 52, 524-30; Vanden Heuvel et al., (1996) Biol Reprod 55, 731-9; Sogawa et al., (1993) Nucleic Acids Res 21, 1527-32; He et al., (1996) Biochemistry 35, 1775-82; Stelzer and Don, J. (2002) Endocrinology 143, 1578-88; Persengiev et al., (1996) Endocrinology 137, 638-646.) (FIG. 5).

It is further contemplated that interactions with distinct co-regulators also provide a means for differential regulation of SREBP2gc target genes in spermatocytes versus spermatids. For example, it is contemplated that SREBP2gc target promoters containing CREs are selectively up-regulated in round spermatids via CREMτ, while other co-regulator elements (e.g., Y and/or GC box proteins) and their cognate germ cell-enriched factors function in late spermatocytes, as well as potentialy spermatids.

The role of SREBP2gc expression in cholesterol synthesis during spermatogenesis remains unknown. Recent studies have shown that loss or inhibition of dhcr24 function, a terminal reductase in the cholesterol biosynthetic pathway, disrupts spermatogenesis (Singh and Chakravarty, (2003) Reprod Toxicol 17, 37-44; Wechsler et al., (2003) Science 302, 2087). Several cholesterol biosynthesis genes also are specifically up-regulated during late spermatogenesis (Teruya et al., (1991) Biol Reprod 44, 663-71; Tacer et al., (2002) J Lipid Res 43, 82-9), which likely involves trans-activation by SREBP2gc. However, a number of observations suggest that enhancement of cholesterol synthesis per se is not the role of this transcription factor in meiotic and haploid germ cells. For example, not all cholesterol biosynthetic genes are coordinately up-regulated during late spermatogenesis (Tracer et al., supra). Accordingly, cholesterol synthesis actually declines in pachytene spermatocytes and round spermatids (Potter et al., (1981) J Biol Chem 256, 7150-4), as does testicular cholesterol content during sexual maturation (Tracer et al., supra). The present invention is not limited to a particular mechanism. Indeed, an understanding of the mechanism is not necessary to practice the present invention. Nonetheless, it is contemplated that these facts further suggest that SREBP2gc has major functions distinct from cholesterol synthesis and are consistent with the switch to a sterol-independent mechanism of SREBP2 production in these spermatogenic stages. While this may involve an increased synthesis of certain cholesterol intermediates such as T-MAS (Tracer et al., supra), it is likely that the main role of SREBP2gc is to regulate a totally new set of promoters uniquely expressed in spermatocytes and spermatids. Up-regulation of known cholesterol biosynthetic genes may be ancillary to this main function.

Accordingly, in some embodiments, the present invention provides methods and compositions for use in identifying modulators of SREBP2gc activity. In some embodiments, the activation of proacrosin promoter based gene expression is used as a screening assay to identify modulators of SREBP2gc transcription factor activity. The present invention further provides therapeutic agents (e.g. identified using the drug screening methods of the present invention) for use in modulating fertility (e.g., a contraceptive agents).

Definitions

To facilitate an understanding of the present invention, a number of terms and phrases are defined below:

As used herein, the term "SRE" or "SRE element" refers to a sterol response element. Sterol response elements are nucleic acid sequences found in regulatory regions of genes (e.g., in promoters) that are binding sites for sterol response element binding proteins (SREBPs). Gene expression of genes regulated by SREs is controlled by the presence or absence of binding by SREBPs.

As used herein, the term "proacrosin promoter" refers to a promoter that activates the expression of the proacrosin gene. As used herein, "proacroasin promoter" refers not only to the full length promoter (SEQ ID NO:15), but also to the minimal promoter elements required for transcription activation. In preferred embodiments, minimal promoter elements include one or more SRE elements (e.g., those described by SEQ ID NOs: 1-14).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "reagent(s) capable of specifically detecting SREBP2gc expression" refers to reagents used to detect the expression of SREBP2gc. Examples of suitable reagents include but are not limited to, nucleic acid probes capable of specifically hybridizing to SREBP2gc mRNA or cDNA, and antibodies (e.g., monoclonal antibodies of the present invention).

As used herein, the term "non-human transgenic animal lacking a functional SREBP2gc gene" refers to a non-human animal (preferable a mammal, more preferably a mouse) whose endogenous SREBP2gc gene has been inactivated (e.g., as the result of a "SREBP2gc knockout" or a "SREBP2gc knock-in").

As used herein, the term "SREBP2gc knockout" refers to a non-human animal (e.g., a mouse) lacking a functional SREBP2gc gene. In some embodiments, the entire SREBP2gc gene is deleted. In other embodiments, the gene is inactivated via other means (e.g., deletion of essential portions or inversions of some or all of the SREBP2gc gene). In other embodiments, the SREBP2gc gene is inactivated using antisense inhibition. SREBP2gc knockout include conditional knockouts (e.g., selective inhibition of gene activity). SREBP2gc knockout mice may be made using any suitable method including, but not limited to, those described herein. SREBP2gc genes can also be inactivated via the construction of a "SREBP2gc knock-in" in which the gene is inactivated by the insertion of exogenous DNA into a region of the gene required for function.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample. "Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk-cell lines, the CAD gene that is used in conjunction with CAD-deficient cells and the mammalian hypoxanthine-guanine phosphoribosyl transferase (hprt) gene that is used in conjunction with hprt-cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, disorder of bodily function or otherwise alter a bodily function (e.g., fertility). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

DETAILED DESCRIPTION OF THE INVENTION

The present invention relates to methods and compositions for modulating fertility. In particular the present invention provides cell lines and transgenic animals for use in identifying modulators of SREBP2gc transcription factors. The present invention further provides therapeutic agents that modulate SREBP2gc signaling for use as fertility modulators.

I. Transgenic Animals Expressing or Lacking SREBP2gc and/or Proacrosin Promoter

The present invention contemplates the generation of transgenic animals comprising an exogenous SREBP2gc gene or mutants and variants thereof (e.g., truncations, deletions, insertions, or single nucleotide polymorphisms). In other embodiments, the present invention provides transgenic animals with a knock-out of the SREBP2gc gene. In other embodiments, the present invention provides transgenic animal expressing exogenous wild type or variant (e.g., mutant) proacrosin promoters constructs. In preferred embodiments, the proacrosin promoter construct further comprises a reporter gene for assaying the level of gene expression from the proacrosin promoter.

In preferred embodiments, the transgenic animal displays an altered phenotype (e.g., decreased or increased SREBP2gc/proacrosin signaling) as compared to wild-type animals. Methods for analyzing the presence or absence of such phenotypes include but are not limited to, those disclosed herein.

The transgenic animals of the present invention find use in drug (e.g., fertility modulation) screens, as well as research applications. In some embodiments, test compounds (e.g., a drug that is suspected of being useful to modulate male fertility) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (p1) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

II. Antibodies

The present invention provides isolated antibodies. In preferred embodiments, the present invention provides monoclonal antibodies that specifically bind to an isolated polypeptide comprised of at least five amino acid residues of SREBP2gc. In some embodiments, antibodies find use in research applications, drug screening, and therapeutic applications (e.g., antibodies directed to factors that influence SREBP2gc transcription factor activity).

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against SREBP2gc). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against SREBP2gc) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, SREBP2gc protein (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

In some embodiments, antibodies (e.g., monoclonal antibodies) are humanized. Humanized antibodies are altered in order to make them less immunogenic to humans, e.g., by constructing chimeric antibodies in which a mouse antigen-binding variable domain is coupled to a human constant domain. Humanized antibodies are typically human antibodies in which some CDR residues and possibly some FR residues are substituted by residues from analogous sites in rodent antibodies. Methods for humanizing antibodies are well known in the art and include but are not limited to, those disclosed in U.S. Pat. Nos. 6,054,297, 4,816,567, 6,180,377, 5,871,907, 5,585,089, and 6,180,370, each of which is herein incorporated by reference.

III. Drug Screening

In some embodiments, the present invention provides drug screening assays (e.g., to screen for fertility modulators). In some embodiments, the screening methods of the present invention utilize SREBP2gc. For example, in some embodiments, the present invention provides methods of screening for compounds that alter (e.g., inhibit or enhance) SREBP2gc mediated transcriptional activity (e.g., through the proacrosin promoter). In other embodiments, candidate compounds are antisense agents (e.g., oligonucleotides) directed against SREBP2gc. See below for a discussion of antisense therapy. In other embodiments, candidate compounds are antibodies (e.g., those described above).

The therapeutic agents of the present invention find use in the modulation of male fertility (e.g., through altering signaling through the proacrosin promoter). For example, in some embodiments, inhibitors of SREBP2gc transcription factor activity find use as contraceptive agents. Such agents are administered to men at regular intervals (e.g., daily) to block sperm development. In other embodiments, enhancers of SREBP2gc transcription factor activity are utilized to enhance fertility (e.g., by increasing spermatogenesis).

In one screening method, candidate compounds are evaluated for their ability to alter (e.g., decrease or increase) SREBP2gc expression by contacting a compound with a cell expressing SREBP2gc and then assaying for the effect of the candidate compounds on expression. In some embodiments, the effect of candidate compounds on expression of SREBP2gc is assayed for by detecting the level of SREBP2gc mRNA expressed by the cell. mRNA expression can be detected by any suitable method, including but not limited to, those disclosed herein.

In other embodiments, the effect of candidate compounds is assayed by measuring the level of SREBP2gc expression. The level of polypeptide expressed can be measured using any suitable method, including but not limited to, those disclosed herein.

In some embodiments, in vitro drug screens are performed using purified wild type SREBP2gc and reporter constructs comprising proacrosin promoters. Compounds are screened for their ability to alter (e.g., decrease) the interaction of SREBP2gc with proacrosin and promote gene expression from the proacrosin promoter. Binding of SREBP2gc to the proacrosin promoter is accomplished in any vessel suitable for containing the reactants. In some embodiments, the promoter construct is assayed in vitro. In other embodiments, a cell line comprising either SREBP2gc or a proacrosin reporter gene construct is utilized. Examples of such vessels include microtitre plates, test tubes, petri dishes and microcentrifuge tubes.

In preferred embodiments, reporter gene assays are utilized to screen test compounds. Reporter gene assays involve the use of host cells transfected with vectors encoding a nucleic acid comprising transcriptional control elements (e.g., proacrosin promoters or portions thereof) spliced to a coding sequence for a reporter gene. Therefore, activation of the target gene by SREBP2gc results in activation of the reporter gene product. Test compounds are then screened for their ability to alter expression of the reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, calorimetric, or bioluminescent products of specific substrates (e.g., X-gal and luciferin). Comparisons between compounds of known and unknown activities may be conducted as described above.

In other embodiments, competitive drug screening assays in which neutralizing antibodies capable of binding SREBP2gc transcription factors specifically compete with a test compound for binding to the proacrosin promoter are utilized. In this manner, the antibodies can be used to detect the presence of any compound that shares one or more antigenic determinants with SREBP2gc transcription factor proteins.

In still further embodiments, transgenic animals having altered (e.g., inactivated or overexpressed) exogenous SREBP2gc or proacrosin promoter (e.g., linked to a reporter gene) are utilized in drug screening applications. For example, in some embodiments, compounds are screened for their ability to reduce expression from the proacrosin promoter. In other embodiments, test compounds are screened for their ability to reduce or enhance sperm production or maturation in mice.

In other embodiments, transgenic animals are utilized in the screening of the toxicity of test compounds. Test compounds are administered to the animals and toxicity is monitored using known methods.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In some drug screening embodiments, the present invention provides methods for detection of SREBP2gc. In preferred embodiments, the presence of SREBP2gc protein or mRNA is measured directly. In some embodiments, the absence or decrease in SREBP2gc mRNA or protein is detected in tissue samples. mRNA expression may be measured by any suitable method, involving, but not limited to, hybridization methods, amplification methods, sequencing, array technologies, mass spectroscopy, and the like.

In some embodiments, SREBP2gc protein or a decrease in levels of SREBP2gc protein is detected. Protein expression may be detected by any suitable method. In some embodiments, proteins are detected by binding of an antibody specific for the protein. Any antibody (monoclonal or polyclonal) that specifically detects SREBP2gc may by utilized. Methods for the generation of antibodies are described above.

Antibody binding is detected by techniques known in the art. For example, in some embodiments where SREBP2gc protein is detected in bodily fluids, antibody binding is detected using a suitable technique, including but not limited to, radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays. In other embodiments, where SREBP2gc protein is detected in tissue samples, immunohistochemistry is utilized for the detection of antibody binding.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include, but are not limited to, those described in U.S. Pat. Nos. 5,885,530, 4,981,785, 6,159,750, and 5,358,691, each of which is herein incorporated by reference. In some embodiments, the analysis and presentation of results is also automated. In other embodiments, the immunoassay described in U.S. Pat. Nos. 5,599,677 and 5,672,480, each of which is herein incorporated by reference, is utilized. In other embodiments, proteins are detected by immunohistochemistry.

IV. Fertility Modulators

As described above, in some embodiments, the present invention provides methods and compositions for modulating (e.g., enhancing or decreasing) fertility. In preferred embodiments, therapeutic agents of the present invention modulate fertility by modulating SREBP2gc transcription factor activity (e.g., binding to or activating proacrosin promoters). Exemplary therapeutic agents are described below.

A. Genetic And Transplantation Therapies

The present invention contemplates the use of any genetic manipulation for use in modulating the expression of SREBP2gc. Examples of genetic manipulation include, but are not limited to, delivery of SREBP2gc (e.g., to cells (e.g., sperm progenitor cells), tissues, or subjects). Delivery of nucleic acid construct to cells in vitro or in vivo may be conducted using any suitable method. A suitable method is one that introduces the nucleic acid construct into the cell such that the desired event occurs (e.g., expression of an antisense construct). For example, cells may be transfected ex vivo to increase or induce SREBP2gc expression and the transfected cells may be transplanted to the site of sperm production.

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

B. Antisense and RNAi Therapies

In some embodiments, the present invention targets the expression of SREBP2gc. For example, in some embodiments, the present invention employs compositions comprising oligomeric antisense compounds, particularly oligonucleotides (e.g., those identified in the drug screening methods described above), for use in modulating the function of nucleic acid molecules encoding SREBP2gc, ultimately modulating the amount of SREBP2gc expressed. This is accomplished by providing antisense compounds (e.g., antisense oligonucleotides, siRNA, etc.) that specifically hybridize with one or more nucleic acids encoding SREBP2gc. The specific hybridization of an oligomeric compound with its target nucleic acid interferes with the normal function of the nucleic acid.

i. RNA Interference (RNAi)

In some embodiments, RNAi is utilized to inhibit SREBP2gc function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001;15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

ii. Antisense

In other embodiments, the present invention employs compositions comprising oligomeric antisense compounds, particularly oligonucleotides (e.g., those identified in the drug screening methods described below), for use in modulating the function of nucleic acid molecules encoding SREBP2gc, ultimately modulating the amount of SREBP2gc expressed. This is accomplished by providing antisense compounds that specifically hybridize with one or more nucleic acids encoding SREBP2gc. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of SREBP2gc. In the context of the present invention, "modulation" means either an increase (stimulation) or a decrease (inhibition) in the expression of a gene. For example, expression may be inhibited to potentially prevent tumor metastasis.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a SREBP2gc protein. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O—alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[$(CH_2)_n$O]$_m CH_3$, O$(CH_2)_n$OCH$_3$, O$(CH_2)_n$NH$_2$, O$(CH_2)_n$CH$_3$, O$(CH_2)_n$ONH$_2$, and O$(CH_2)_n$ ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O(CH$_2$)$_2$ON(CH$_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

Other preferred modifications include 2'-methoxy(2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

C. Antibody Therapy

In some embodiments, the present invention provides antibodies that target SREBP2gc. In preferred embodiments, the antibodies are used as fertility inhibitors (e.g., by inhibiting spermatogenesis.

D. Small Molecule Drugs

In some embodiments, the present invention provides drugs (e.g., small molecule drugs) that alter (e.g., inhibit) fertility by modulating sperm development. In preferred embodiments, the drugs alter the biological activity of SREBP2gc or its interaction with the proacrosin promoter. In some embodiments, small molecule drugs are identified using the drug screening methods described above.

E. Pharmaceutical Compositions

The present invention further provides pharmaceutical compositions (e.g., comprising the therapeutic compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the state to be treated, with the course of treatment lasting from several days to several months, or until the desired result is achieved (e.g., decreased sperm count). Optimal dosing schedules can be calculated from measurements of drug accumulation in the body of the patient. The administering physician can easily determine optimum dosages, dosing methodologies and repetition rates. Optimum dosages may vary depending on the relative potency of individual drugs, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

Experimental

The following examples are provided in order to demonstrate and further illustrate certain preferred embodiments and aspects of the present invention and are not to be construed as limiting the scope thereof.

A. Materials and Methods

Plasmids DNA constructs. A ~1 kb genomic fragment containing 5'- flanking, exon1, intron1 and partial exon 2 sequences for the rat proacrosin gene (Genebank number X58550) (SEQ ID NO:15) was generated by PCR (5' GCCA-GAGAAATCAAGATTATCCCATCAG 3'(SEQ ID NO:16) and 5' TCCTGCCCTAACCTGGCCTGCAAGCTGT 3 (SEQ ID NO:17). This was inserted into pGEM-T easy vector (Promega, Madison, Wis.), then released with Sad and SacII and subcloned into pGL3-Basic vector using Sad and Smal sites. This step eliminates a polylinker region within the pGL3-Basic plasmid that contains an E-box responsive to SREBPs (Annicotte et al., (2001) Biotechniques 31, 993-4, 996). Additional proacrosin promoter constructs containing mutations in SREBP2gc binding sites were generated by PCR.

RNA and protein analyses. Total RNAs were prepared and analyzed by Northern analysis and RTPCR as previously described (Wang et al., supra). Nuclear extracts were prepared from cell lines and enriched mouse spermatogenic cells using high salt extraction (Liu et al., (1997) J Biol Chem 272, 5056-62). The oligodeoxynucleotides used for generating various DNA probes and competitors for electrophoretic mobility shift assays (EMSAs) as well as primers for RT-PCR are listed in Table 1. EMSAs were performed using an SRE-1 probe, as employed in previous studies of SREBP2gc (Wang et al., supra).

TABLE I

Oligonucleotides Used in PCR and EMSA Analysis.

| | Rat Proacrosin Promoter | SEQ ID NO | Position* |
|---|---|---|---|
| Sense | 5' GCCAGAGAAATCAAGATTATCCCATCAG 3' | 18 | −982 to −1010 |
| antisense | 5' TCCTGCCCTAACCTGGCCTGCAAGCTGT 3' | 19 | −2 to −31 |
| | Mutated Proacrosin Promoter Constructs | | |
| P 1-1 | 5' ACTAGTGATTGCCAGAGA 3' | 20 | −1002 to −1010, sense (underlined) |
| P 1-2 | 5' CTTATCTTATCTAATTTTATTTTCCCCTGTATGTTGA 3' | 21 | −838 to −861, (underlined) |
| P 1-3 | 5' GAAAATAAAATTAGATAAGATAAGCATTCTCATCTCGTGACG 3' | 22 | −803 to −821, sense |
| P 1-4 | 5' TATCTTCTATCTTATCCTAACATCTCCTCTAGGGGCGT 3' | 23 | −786 to −805, antisense |
| P 1-5 | 5' AGGATAAGATAGAAGATACGGGTGGGGACTCACAGC 3' | 24 | −746 to −763, sense |
| P 1-6 | 5' GGGGTTACCAGAACACTTTCAAGG 3' | 25 | −436 to −459, antisense |
| P 2-1 | 5' GTCGGTATCATCCTCCACAG 3' | 26 | −287 to −306, sense |
| P 2-2 | 5' TATCTTATCCTTCTGACGTCTCACTTTATG 3' | 27 | −249 to −269, antisense |
| P 2-3 | 5' CGTCAGAAGGATAAGATAGGATGAATGAAGGTCTTAG 3' | 28 | −211 to −239, sense |
| P 2-4 | 5' TATCGGTATCTTATATCTTATCGACCAACCCGTTTCCTCA 3' | 29 | −198 to −217, antisense |
| P 2-5 | 5' GATAAGATATAAGATACCGATACGGGAGAATTCACGCAGGAG 3' | 30 | −153 to −172, sense |
| P 2-6 | 5' GCCTTCTGGCCAATCAGCAG 3' | 31 | −51 to −70, antisense |
| | EMSA | | |
| SREpa1 | 5' GATCTGCACCTCAGTA 3' | 32 | −135 to −143, sense (underlined) |
| | 5' TACTGAGGTGCA 3' | 33 | antisense |
| SREpa2 | 5' TTGGTCGCTCATGAGTACCTCACC 3' | 34 | −182 to −205, sense (underlined) |
| | 5' CAACCGGTGGTGAGGTACTCATGAGC 3' | 35 | −182 to −199, antisense |
| SREpa2 MUT | 5' GATCTAATAAGATATAATAAG 3' | 36 | sense |
| | 5' TGCATATCTTATTATATC 3' | 37 | antisense |
| SREpa3 | 5' GATCGGCTCGCCAATG 3' | 38 | −240 to −248, sense (underlined) |
| | 5' TGCATTGGCGAGCC 3' | 39 | antisense |
| SREpa3 MUT | 5' GAAGGATAAGATAGG 3' | 40 | sense |
| | 5' ATCCTATCTTATCCT 3' | 41 | antisense |
| SREpa4 | 5' AGCCTTTCCATGCTA 3' | 42 | −771 to −785, sense |
| | 5' TTATAGCATGGAAAG 3' | 43 | antisense |

TABLE I-continued

Oligonucleotides Used in PCR and EMSA Analysis.

| | Rat Proacrosin Promoter | SEQ ID NO | Position* |
|---|---|---|---|
| SREpa5 | 5' TGTCTCGATGGGTAG 3' | 44 | −824 to −838, sense |
| | 5' CTCCTACCCATCGAG 3' | 45 | antisense |
| SREpa4 & 5 MUT | 5' GATCTGATTTGA 3' | 46 | sense |
| | 5' TGCATATCTTATCAG 3' | 47 | antisense |
| Luciferase | 5' ATACGCCCTGGTTCCTG 3' | 48 | sense |
| | 5' AATGCCCATACTGTTGAGC 3' | 49 | antisense |

*numbers indicate the position of the rat proacrosin promoter nucleotide sequence (Gene Bank number X58550), translational-start site is +1. Mutant bases are italicized.

Cell cultures and transfections. Cell lines were cultured in Dulbecco's Modified Eagle's medium containing 10% fetal bovine serum (FBS) and 100 units/ml penicillin-streptomycin, and GC-1spc cells were cultured in 13% FBS. One percent non-essential amino acids also were included for GC-4spc and GC-1spc cells. All cells were incubated with 5% $CO_2$ at 37° C. For promoter studies, DNAs for promoter constructs (0.5 μg), pCMV7 or pCMV-BP2gc (10 ng) and pCMV-lacZ or pRL-null normalization plasmids (0.1 μg) were co-transfected using Trans-Fast transfection reagent (Promega, Madison, Wis.). Cell extracts were then analyzed 40-48 hrs later with commercial kits for β-galactosidase (Tropix, Bedford, Mass.) and luciferase activities (Promega). The expression vector pKAc (0.1 μg) for the protein kinase A c-subunit also was included in proacrosin promoter studies. Student's t-test was used to evaluate data significance.

Transgenic mice. Transgenes containing wild-type or mutant rat proacrosin promoter-luciferase sequences as well as an SV40 poly (A) signal were released from their parent pGL3 vectors using SalI and ApaI and gel purified prior to injection. The genotype of offspring was determined by PCR for luciferase sequences (Table 1). Testes and somatic tissues from adult (2-3 months) male transgenic founders or F1 mice were extracted and assayed for luciferase activity. Protein concentration was determined using Bradford reagent (Bio-Rad Laboratory, Hercules, Calif.).

Immunohistochemistry. Immunostaining was performed on paraffin embedded sections of adult mouse testes as described in previous studies (Agustin et al., (2000) Mol Biol Cell 11, 3031-44) with slight modifications. Briefly, deparaffinized testes sections (5 μm) were rehydrated, subjected to antigen retrieval and blocking using the biotin blocking system (DakoCytomation, Carpenteria, Calif.) and 20% normal swine serum/5% fatty acid free-BSA. Sections were incubated with rabbit anti-luciferase antibody (0.5 μg/ml) (Cortex Biochem INC, San Leandro, Calif.) and bound antibody was detected using biotinylated swine anti-rabbit immunoglobulin G and alkaline phosphatase-conjugated streptavidin together with the Fuchsin Substrate System (DakoCytomation). Hematoxylin was used as a counterstain.

Promoter sequence analysis. To identify possible SREBP2gc response elements within the rat, mouse and human proacrosin promoters, sequences obtained from Gen-Bank were searched for known SRE half-sites using OMIGA 2.0 software (Oxford Molecular Ltd). These were also compared to a NNCNNNCNAN motif often associated with SREs (Swinnen et al., (1998) J Biol Chem 273, 19938-44).

B. Results

SREBP2gc is expressed in a spermatogenic cell line. To test the hypothesis that SREBP2gc mediates spermatogenic cell-specific gene expression, the expression of SREBP2gc in cell lines derived from male germ cells was investigated. GC-4spc cells were originally selected using a neomycin resistance expression vector driven by the human pgk-2 promoter (Tascou et al., (2000) Biol Reprod 63, 1555-61). They express several spermatocyte-related genes, including proacrosin and pgk-2, but not various markers for testicular somatic cells nor a spermatogonia-associated gene promoter. Northern and RT-PCR analyses of GC-4spc cells detected an SREBP2gc mRNA that was identical in size (~2.5 kb) and similar in amount to that for the adult mouse germ cell transcript (FIG. 1 A,B). GC-4spc cells also contain substantial amounts of sequence-specific sterol response element (SRE) binding activity based on EMSAs (FIG. 1C). This binding activity was present even though GC-4spc cells were cultured under serum containing (sterol-loaded) conditions, which suppress formation of transcriptionally active SREBPs in somatic cells due to feedback inhibition of precursor processing (Wang et al., supra). Thus, SRE binding activity in GC-4spc cells is uniquely insensitive to sterols, consistent with the properties of SREBP2gc in spermatogenic cells (Wang et al., supra).

Figure 2:
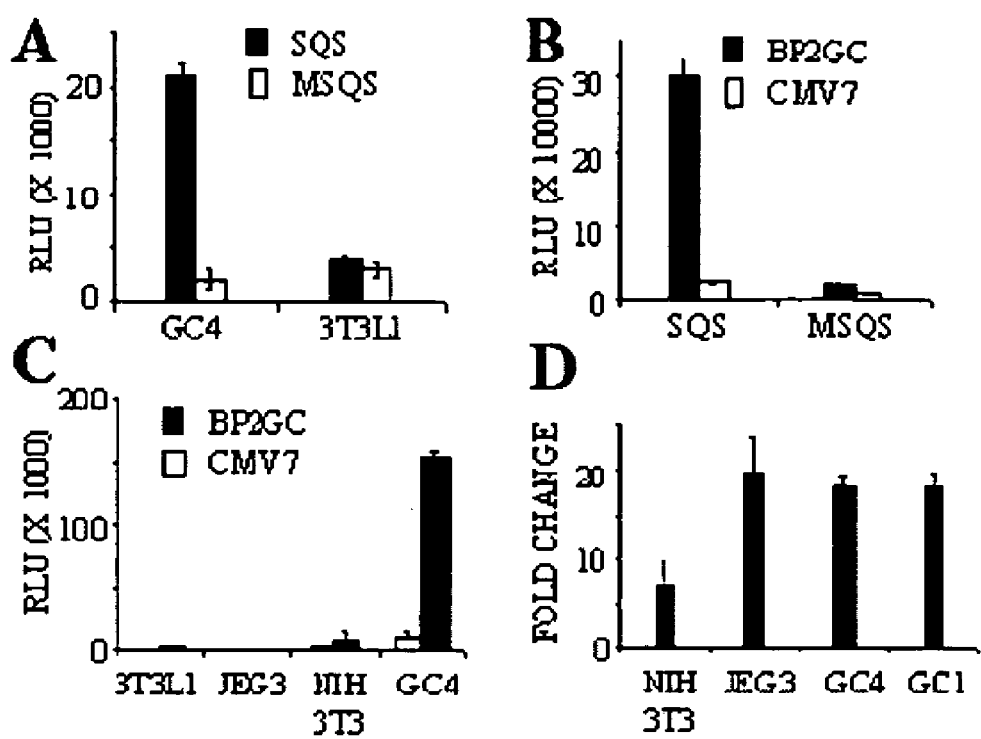
FIG. 2 shows expression of SREBP transcriptional activity in GC-4spc cells.

To examine whether GC-4spc cells express endogenous SRE-dependent transcriptional activity, they were transfected with squalene synthase (SQS) promoter-luciferase plasmids (Guan et al., (1998) J Biol Chem 273, 12526-35). The SQS gene is responsive to SREBPs and is expressed in spermatocytes as well as spermatids (Stromstedt et al., (1998) Endocrinology 139, 2314-21). Much higher basal SQS promoter activity was observed in GC-4spc relative to somatic cell lines such as 3T3-L1 (FIG. 2A), which lack detectable SREBPs under serum (+) conditions (Wang et al., supra). Basal promoter activity in GC-4spc cells was highly dependent on a functional SRE site (>10-fold difference between wild-type and SRE-mutant constructs), which was not the case in transfected 3T3L1 cells (FIG. 2A). This indicated the presence of endogenous SREBP transcriptional activity selectively in GC-4spc cells. Further, co-transfected SREBP2gc dramatically increased SQS promoter activity in GC-4spc cells, which also required the SRE site (FIG. 2B). Thus, GC-4spc cells express SREBP2gc and are suitable for studying its transcriptional activity in a spermatogenic cell like environment, including its possible regulation of germ cell-specific gene expression.

SREBP2gc activates a spermatogenic cell-specific promoter. Proacrosin is an acrosomal zymogen for a protease implicated in sperm competition and sperm-oocyte interactions (Adham et al., (1997) Mol Reprod Dev 46, 370-6; Nayernia et al., (2003) Cytogenet Genome Res 103, 314-20.) and in the dispersal of acrosomal components upon onset of the acrosome reaction (Yamagata et al., (1998) J Biol Chem 273, 10470-4.). It is a spermatogenic cell-specific gene first expressed in spermatocytes and then highly up-regulated in spermatids (Kashiwabara et al., (1990) Biochem Biophys Res Commun 173, 240-5.), at which time mRNA translation occurs (Nayernia et al., (1994) Biochem Biophys Res Commun 202, 88-93). Since both the proacrosin and pgk-2 promoters are transcribed in pachytene spermatocytes and in GC-4spc cells, their regulation by SREBP2gc was examined in co-transfection studies. Pgk-2 promoter activity was not stimulated by SREBP2gc in any of the cell lines tested. Strong activation of the proacrosin promoter was observed in GC-4spc cells (FIG. 2C). This promoter was poorly expressed or undetectable in somatic cell lines, and no significant stimulation by SREBP2gc was observed in any of these (FIG. 2C). SREBP2gc also did not activate the proacrosin promoter in a different spermatogenic cell-derived cell line, GC-1spg, which resembles late spermatogonial stages and does not express the proacrosin promoter (Tascou et al., (2000) Biol Reprod 63, 1555-61; Hofmann et al., (1992) Exper. Cell Res. 201, 417-435). More generally expressed SREBP target promoters (CYP51 (Rozman et al., (1999) Mol Endocrinol 13, 1951-62) or SQS) were strongly activated by SREBP2gc in all cell lines tested (FIG. 2D), demonstrating that the co-transfected factor is transcriptionally active in each case. Thus, SREBP2gc potently activates the proacrosin promoter in a cell-specific manner.

Figure 3:
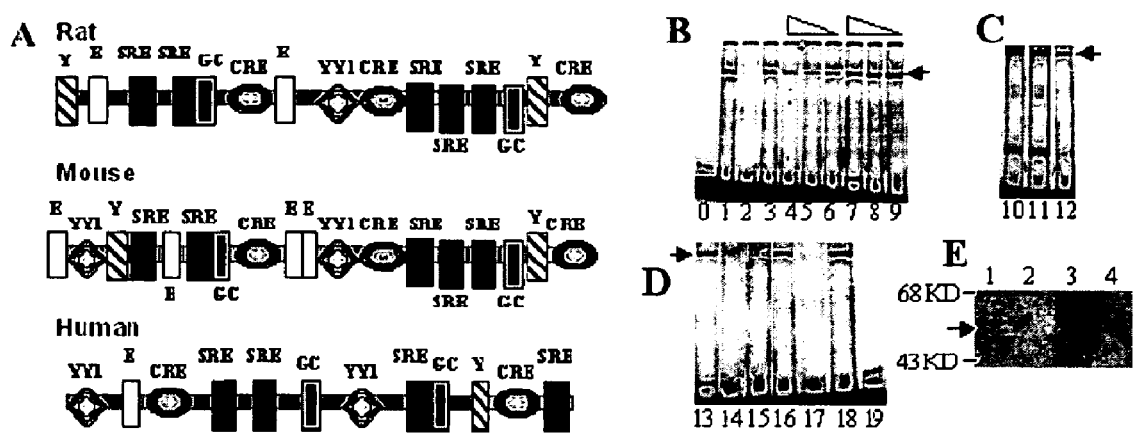
FIG. 3 shows SREBP2gc binding sites within the proacrosin promoter.

The proacrosin promoter contains SREBP2gc response elements. The rat and mouse proacrosin promoters are highly homologous and contain a number of conserved trans-factor consensus elements (Kremling et al., (1991) Genomics 11, 828-34; Schulten et al., (2001) J Cell Biochem 83, 155-62) (FIG. 3A). These include sites for known SREBP co-regulators: Y boxes, cyclic AMP response elements (CREs), YY1 sites and GC-boxes. A search for SRE-like sequences identified five potential SREBP2gc response elements within the rat and mouse proacrosin promoters that were conserved in their locations and general sequence features (SREpa1-5; FIG. 3A, Table I). In most instances, two or more previously identified SRE half-sites were present, and several contained an NNCNNNCNAN motif found in several SREs (Swinnen et al., (1998) J Biol Chem 273, 19938-44). The presence of multiple SREs within a target promoter is not uncommon (Ikeda et al., (2001) J Biol Chem 276, 34259-69). The SREpas for the rat and mouse were segregated into upstream (SREpa4 and 5) and downstream (SREpa1,2 and 3) groups that were closely adjacent to consensus sequences for known co-regulators (FIG. 3A). Such close proximity of SREs and coregulator sites is typical for SREBP-responsive promoters (Shimano, (2001) Prog Lipid Res 40, 439-52.). Multiple SRE-like sequences along with neighboring co-regulator sites also were identified in the human proacrosin promoter (FIG. 3A, Table I), suggesting conservation of promoter organization in humans.

Competition EMSAs were performed on candidate SREs for the rat proacrosin promoter using mouse germ cell extracts. All but one (SREpa1) exhibited good binding to native SREBP2gc (FIG. 3B-D). Mutated versions of these four rat SREpas showed greatly diminished binding. Southwestern analysis previously demonstrated that the 55 kDa SREBP2gc protein in spermatogenic cells bound to SRE sequences (Wang et al., supra). This assay confirmed the binding of rat proacrosin SRE sites by endogenous SREBP2gc in mouse germ cell extracts (FIG. 3E).

Figure 4:
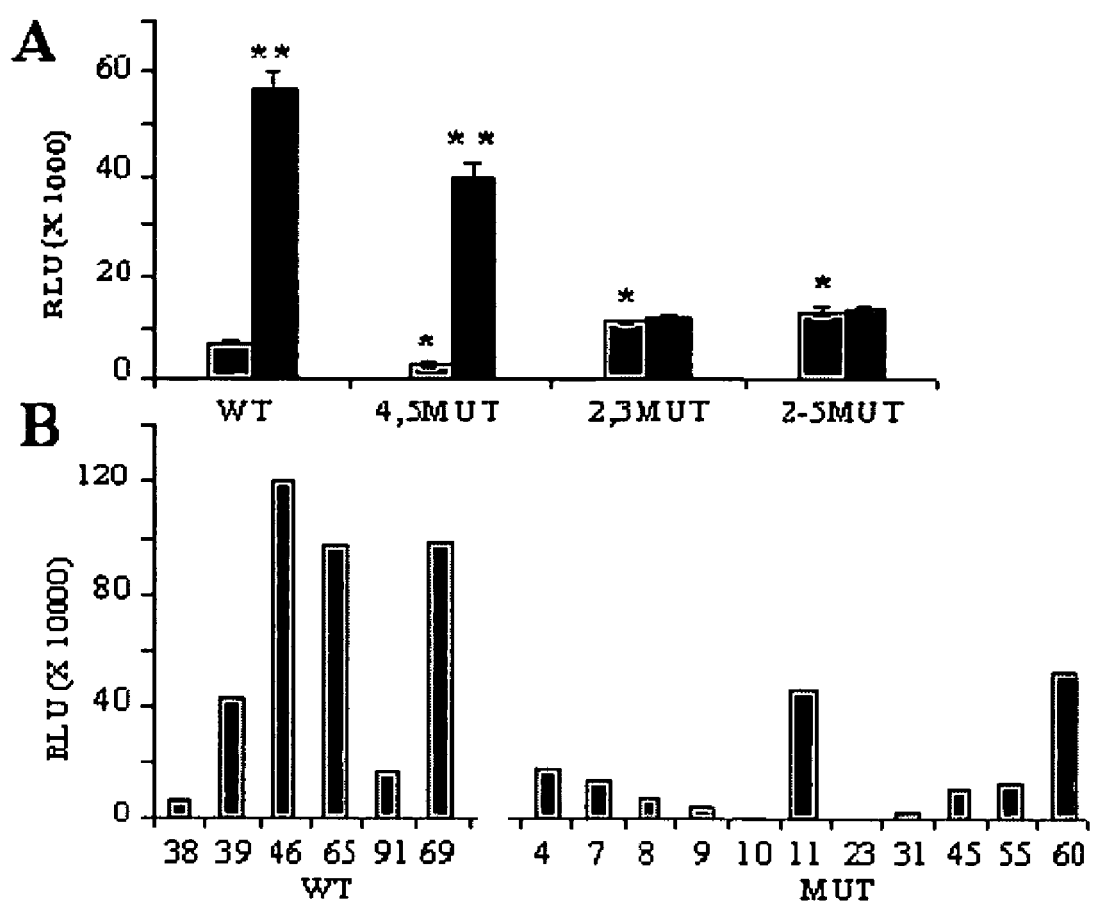
FIG. 4 shows that SREBP2gc binding sites are required for proacrosin promoter activation in vitro and in vivo.

The functional importance of the SREpa sites was examined by promoter mutation analysis. Three different rat proacrosin promoter constructs were generated, two in which either the upstream sites (SREpa4, 5mut) or the downstream sites (SREpa2,3mut) were mutated, and a third containing mutations of all four sites (SREpa2-5mut). These promoters were then tested in GC-4spc cells for basal and SREBP2gc-stimulated activities (FIG. 4A). Mutation of the two upstream SREpas reduced basal activity ~3-fold, while activation by SREBP2gc was only modestly affected. Mutation of the downstream SREpa2 and 3 sites resulted in complete loss of SREBP2gc induced activation (FIG. 4A). The combined upstream and downstream promoter mutant also showed no SREBP2gc-dependent stimulation. Thus, SREpa2 and 3 are critical for SREBP2gc induction of the proacrosin promoter in GC-4spc cells. SREpa4 and 5 are required for optimal basal promoter activation by endogenous SREBP2gc. Mutation of either SREpa2 and 3 alone or of all four sites caused a small increase in basal activity (FIG. 4A).

In vivo expression of the proacrosin promoter depends on SREBP2gc response elements. To test the importance of SREBP2gc-induced activation in proacrosin promoter expression during spermatogenesis, transgenic mice harboring wild-type or SREpa-mutant proacrosin-luciferase fusion genes were generated. The SREpa2-5mut promoter was examined to test the cumulative role of all SREBP2gc response elements. Previous studies showed that the ~1-kb rat proacrosin promoter used here directed faithful cell-specific gene expression in spermatocytes and spermatids of transgenic mice (Nayernia et al., (1994) J. Biol. Chem. 269, 32181-32186). Out of six transgenic males containing wild-type rat proacrosin promoter sequences, four expressed moderate-to-high levels of luciferase activity in the testis, while two exhibited low activity (FIG. 4B). This expression frequency (67%) is typical for active transgene promoters (Palmiter and Brinster, (1986) Annu Rev Genet 20, 465-99; Liu et al., (1997) J Biol Chem 272, 5056-62). No activity was detected in somatic tissues from any transgenic mice. In contrast, the SREpa2-5 mutant promoter was expressed at much lower levels in testes of founder males, with only 18% (2/11) having moderate testicular expression and none showing high expression.

Immunohistochemical staining for luciferase protein confirmed strong transgene expression in round spermatids of mice expressing the wild-type proacrosin promoter, with the strongest staining occurring in stages VI-VII. Luciferase expression also was detected in late, condensing spermatids. No staining was discernable in spermatocyte stages, consistent with stage-dependent translational regulation of endogenous proacrosin mRNA and proacrosin transgene derived transcripts (Nayernia et al., (1994) Biochem Biophys Res Commun 202, 88-93; Nayernia et al., (1994) J. Biol. Chem. 269, 32181-32186). No transgene expression was detectable in testicular somatic cell types (peritubular, Sertoli and interstitial cells). In contrast, transgene expression was very weak in all spermatid stages of mice expressing the SREpa2-5mut proacrosin promoter. Thus, SREBP2gc response elements are important for proacrosin promoter expression during spermatogenesis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of screening one or more test compounds that alter the interaction of SREBP2gc with a proacrosin promoter, comprising:
   a) providing
      i) a nucleic acid sequence comprising a proacrosin promoter operably linked to a reporter gene;
      ii) a SREBP2gc polypeptide; and
      iii) one or more test compounds;
   b) contacting said proacrosin promoter and said SREBP2gc polypeptide with said one or more test compounds in vitro; and
   c) measuring expression of said reporter gene in the presence of said one or more test compounds and in the absence of said one or more test compounds, wherein a difference in expression indicates that said one or more test compounds alters the interaction of said SREBP2gc polypeptide with said proacrosin promoter.

2. The method of claim 1, wherein said one or more test compounds decrease reporter gene expression.

3. The method of claim 1, wherein said SREBP2gc polypeptide is produced by expression of a nucleic acid encoding said SREBP2gc polypeptide.

4. The method of claim 1, wherein said proacrosin promoter comprises the nucleic acid sequence of SEQ ID NO: 15.

5. The method of claim 1, wherein said proacrosin promoter comprises one or more sterol response elements.

6. The method of claim 5, wherein said sterol response elements are mutant sterol response elements.

7. The method of claim 6, wherein said mutant sterol response elements are non-functional.

8. A method of screening one or more test compounds that alter the interaction of SREBP2gc with a proacrosin promoter, comprising:
   a) providing a cell that comprises
      i) a nucleic acid sequence comprising a proacrosin promoter operably linked to a reporter gene; and
      ii) a nucleic acid sequence encoding a SREBP2gc polypeptide;
   b) providing one or more test compounds;
   c) contacting said cell with said one or more test compounds in vitro; and
   d) measuring expression of said reporter gene in the presence of said one or more test compounds and in the absence of said one or more test compounds, wherein a difference in expression indicates that said one or more test compounds alters the interaction of said SREBP2gc polypeptide with said proacrosin promoter.

9. The method of claim 8, wherein said cell is a spermatocyte.

10. The method of claim 9, wherein said spermatocyte is from a GC-4spc cell line.

11. The method of claim 8, wherein said one or more test compounds decrease.

12. The method of claim 8, wherein said proacrosin promoter comprises the nucleic acid sequence of SEQ ID NO: 15.

13. The method of claim 8, wherein said proacrosin promoter comprises one or more sterol response elements.

14. The method of claim 13, wherein said sterol response elements are mutant sterol response elements.

15. The method of claim 14, wherein said mutant sterol response elements are non-functional.

16. The method of claim 1, wherein said SREBP2gc polypeptide competes with said one or more test compounds for specific binding to said proacrosin promoter.

17. The method of claim 8, wherein said SREBP2gc polypeptide competes with said one or more test compounds for specific binding to said proacrosin promoter.

18. A method of screening one or more test compounds that alter the interaction of SREBP2gc with a proacrosin promoter, comprising:
   a) providing
      i) a nucleic acid sequence comprising a proacrosin promoter operably linked to a reporter gene;
      ii) a SREBP2gc polypeptide; and
      iii) one or more test compounds;
   b) contacting said proacrosin promoter or said SREBP2gc polypeptide with said one or more test compounds in vitro; and
   c) measuring expression of said reporter gene in the presence of said one or more test compounds and in the absence of said one or more test compounds, wherein a difference in expression indicates that said one or more test compounds alters the interaction of said SREBP2gc polypeptide with said proacrosin promoter.

* * * * *

UNITED STATES PATENT AND TRADEMARK OFFICE
CERTIFICATE OF CORRECTION

PATENT NO. : 7,794,951 B2
APPLICATION NO. : 11/253012
DATED : September 14, 2010
INVENTOR(S) : Daniel Kilpatrick and Hang Wang It is certified that error appears in the above-identified patent and that said Letters Patent is hereby corrected as shown below:

Page Ten, column one, lines four through seven (4-7) prior to the "FIELD OF THE INVENTION" section, please insert the following language in place of the current paragraph:

--This invention was made with Government support under grant numbers DK036468 and DK032520 awarded by the National Institutes of Health. The Government has certain rights in the invention.--

Signed and Sealed this

Thirtieth Day of November, 2010

David J. Kappos
*Director of the United States Patent and Trademark Office*

SEQUENCE LISTING

<160> NUMBER OF SEQ ID NOS: 49

<210> SEQ ID NO 1
<211> LENGTH: 19
<212> TYPE: DNA
<213> ORGANISM: Mus musculus

<400> SEQUENCE: 1
gcacttcagc acagatcag                                                 19

<210> SEQ ID NO 2
<211> LENGTH: 13
<212> TYPE: DNA
<213> ORGANISM: Rattus norvegicus

<400> SEQUENCE: 2
tggcacctca gcg                                                       13

<210> SEQ ID NO 3
<211> LENGTH: 43
<212> TYPE: DNA
<213> ORGANISM: Mus musculus

<400> SEQUENCE: 3
atgggttggt tgcacatgag taccttcacc accctgaggt cag                      43

<210> SEQ ID NO 4
<211> LENGTH: 29
<212> TYPE: DNA
<213> ORGANISM: Rattus norvegicus

<400> SEQUENCE: 4
ctcatgagta cctcaccacc ctgaggcgg                                      29

<210> SEQ ID NO 5
<211> LENGTH: 10
<212> TYPE: DNA
<213> ORGANISM: Mus musculus

<400> SEQUENCE: 5
ggctggccaa                                                           10

<210> SEQ ID NO 6
<211> LENGTH: 10
<212> TYPE: DNA
<213> ORGANISM: Rattus norvegicus

<400> SEQUENCE: 6
ggctcgccaa                                                           10

<210> SEQ ID NO 7
<211> LENGTH: 15
<212> TYPE: DNA
<213> ORGANISM: Mus musculus

```
<400> SEQUENCE: 7
acctttccat actat                                                    15

<210> SEQ ID NO 8
<211> LENGTH: 21
<212> TYPE: DNA
<213> ORGANISM: Rattus norvegicus

<400> SEQUENCE: 8
gcctttccat gctataagag g                                             21

<210> SEQ ID NO 9
<211> LENGTH: 14
<212> TYPE: DNA
<213> ORGANISM: Mus musculus

<400> SEQUENCE: 9
ctggatgggt agga                                                     14

<210> SEQ ID NO 10
<211> LENGTH: 16
<212> TYPE: DNA
<213> ORGANISM: Rattus norvegicus

<400> SEQUENCE: 10
gtctcgatgg gtagga                                                   16

<210> SEQ ID NO 11
<211> LENGTH: 13
<212> TYPE: DNA
<213> ORGANISM: Homo sapiens

<400> SEQUENCE: 11
ttgcaggcca ggc                                                      13

<210> SEQ ID NO 12
<211> LENGTH: 13
<212> TYPE: DNA
<213> ORGANISM: Homo sapiens

<400> SEQUENCE: 12
acctggcctg act                                                      13

<210> SEQ ID NO 13
<211> LENGTH: 13
<212> TYPE: DNA
<213> ORGANISM: Homo sapiens

<400> SEQUENCE: 13
gggtgatgtg ggg                                                      13

<210> SEQ ID NO 14
<211> LENGTH: 13
<212> TYPE: DNA
<213> ORGANISM: Homo sapiens

<400> SEQUENCE: 14
gtctgcagtg gac                                                      13

<210> SEQ ID NO 15
<211> LENGTH: 3754
<212> TYPE: DNA
<213> ORGANISM: Rattus sp.
```

```
<220> FEATURE:
<221> NAME/KEY: misc_feature
<222> LOCATION: (1790)..(1794)
<223> OTHER INFORMATION: n is a, c, g, or t
<220> FEATURE:
<221> NAME/KEY: misc_feature
<222> LOCATION: (2226)..(2231)
<223> OTHER INFORMATION: n is a, c, g, or t
<220> FEATURE:
<221> NAME/KEY: misc_feature
<222> LOCATION: (2695)..(2699)
<223> OTHER INFORMATION: n is a, c, g, or t
<220> FEATURE:
<221> NAME/KEY: misc_feature
<222> LOCATION: (2909)..(2914)
<223> OTHER INFORMATION: n is a, c, g, or t

<400> SEQUENCE: 15
tgaagtaaga cattcagtta aatgtgccag agaaatcaag attatcccat cagggattgg      60
ggatttagct cagtggtaga gcgcttgcct agcaagcaca aggccctggg tttggtcccc     120
agttcagaaa aaagagaaa gagaaaaaaa aagattatcc catcaaatga gaactcaaca      180
tacaggggaa aataaaatgt ctcgatgggt aggagcattc tcatctcgtg acgcccctag     240
aggagatgtt agccttttcca tgctataaga ggcgggtggg gactcacagc taaggggaga    300
ggataccttc tgacattgtt actgggaaag aggagcatca tagtacgtgg cacgcacctg    360
tcatactgtc ttctgataat cagatatgta taaataaga cgcttgctac tcaggtagcc     420
gtgacaagaa ttccgctgct cgagtataga cgctcctgtg tggctgtact tgtgtacaaa    480
agaggagacc cggagaactt caagaagtat gtgatactca gaaatgggca agaaggtagg    540
ctttgaaatc ataagtcaag aaacttcaaa atggctcctt gaaagtgttc tggtaacccc     600
cccccccccc cccctgtac tgatgatccc atcagtcagc agaacccgat ttcttttcga     660
tgtgaacatc tcggatgtat tacctcatta caggagggcc gagctgctct tcagaccgtg     720
agccctgttg tcggtatcat cctccacaga gcatatccca acattcata aagtgagacg      780 tcagaaggct cgccaaggat gaatgaaggt cttaggactg aggaaacggg ttggtcgctc     840
atgagtacct caccaccctg aggcgggaga attcacgcag gaggtttgga tggcacctca    900
gcgtggatca gttagtcgag gaggcctgcc tggcctaact gctggggtgg gggtgggaga    960
tcaccctgct gattggccag aaggctgcag agctttgtga ggtcacagct tgcaggccag   1020
gttagggcag gagtatggta gagatgctgc caactgtcgt tgcgctggtc ctggcagtgt   1080
ccgtggttgc caaggataac accacgtgtg agtaagtgtt gggcaccttg gtgggtgctc   1140
atgaataaca ggtcctatcc agacgccctc tgtccgggct agagtgagta gcacattgcc   1200
tttgcaggct ctggatagtt tcatagttcc tgtgatccac atcccagtt cagatccttc    1260 ctgcttccag aactgtgatc ctagaatcat taggtttcca gctgcccctg gcttcccagg   1320 aaggtgggt gaggggtgag gatgacccat tattcctaga tctcttccca ctacctcagt    1380
gactgacttc cttgcctgtc aggtatcggg gcctaaactt tgggagcccc tgttctcctc   1440
tggatgattg aggtcaatca cctgtgtgtg aattcaaagg actgctactc ctttgcacct   1500
ctattccacc cgaagactct cattcctaag ggactcacaa tgcaaacaac tctaaactct   1560
aggtggcctc cccccacccc ccataagtcc ccagaacttc cggctcagat cccctcttct   1620
tcttgtgtga ttctaatgct catgagacac tgtatttgcg tgcaattatc tgcagttaag   1680
atctcagacc cagctccaca gtttctacaa cctccttagt catgtgacat ttgcctgagt   1740
ctccatccaa gattggtctg aaaaccatta cacctctccg aagcactttn nnnngactgt   1800
```

```
gcctcctcaa tccctaggct gcctgcctcc cccaggtgtg gaggtacaaa gactgatgcc    1860
tcttcttggt ttgagcagtt tcctggtctc tcctcagtgg cccctgtgga ttacgattca    1920
ggcagaaccc tcaagcaggt atccggattg tcggagggca gacttcgtcg cgctgggcct    1980
ggccctggat ggtcagttta cagatcttca cgtcccataa cagccgtagg tatcacgcct    2040
gcggaggcag cctactgaac tcccactggg tgctcacggc tgctcactgc ttcgataaca    2100
aaaagtaggt gtggggctca gagagggagg tctctagggt aaccttcacg gacagggagt    2160
cccccagagt ctctgtggag ctctgggacc acatggtcac cagactccaa aggctctgag    2220
gtcgannnnn nctggggacc ttttctccca cagaaaagtc tatgactgga gactggtttt    2280
tggagcccat gaaattgaat acggaagaaa caagccagtg aaagagcccc agcaggaaag    2340
atacgtgcag aaaattgtca tccacgagaa atacaacgct gtgaccgagg ggaacgacat    2400
tgccctcttg aaagtcactc ctcctgttac atgtggggac ttcgttgggc ctggctgcct    2460
acctcatttt aagtctggtc ctcccagaat cccccacacc tgctacgtga ctgggtgggg    2520
atacataaaa gataacggtg agtatatgct gggctcctcg gtgggcactg gcgcccattc    2580
tccttgctgg ctgtctttgc acggcaaggg tcacgatgtg tggctaagct gttttactcc    2640
tctcagcatc atgaatagag tctggcacag acccttcat ggctgagaga attcnnnnnc    2700
tgacggctgt gtgcctgcg cagcccccag accatcacct gtcctgatgg aggcccgagt    2760
ggatctcatt gacctcgacc tgtgtaactc cacccagtgg tacaatgggc gtgtcacatc    2820
aactaatgtg tgcgcagggt atcctgaagg caagattgac acctgccagg taacttcctt    2880
ctgtacccca gacccttggt cctcttgann nnnncgtata tttgcaacac tcaaccttac    2940
cagttgagtc taaggcaggc aggaaactat gtgggctggc attgttctcc catagcccca    3000
tgagccttct gggaagggag agtggttcag gctgaaagtg acccctctgt cctctgacag    3060
ggggacagtg gtgggcctct catgtgcaga gacacgcgtc gacagcccct tgtgatcgt     3120 ggggatcacg agctgggggg taggctgtgc cgtgctaagc gtcctggagt ctacacagcc    3180
acctgggact acctggactg gattgcttcc aagatcggcc ctaccgcctt gcacttgatt    3240
cagccggcca cccctcaccc acctacaacc cagcaaccgg tcatctcttt ccaccctcct    3300
tcgactccac cctccttggt acttccaaca cctgtctcct cggccgcttt acctacgccg    3360
cctcggcctc tgctccatca gccgtcttca gtccatacct cctcagctcc agtcataccct   3420 ctactctccc tgctcacccc agtccagcct gtgtccttta cccttgctgc gtaccacaca    3480
aggcaccaca caacgctgtc ttttgcttcg gcgttacagc atctcataga ggccctgaag    3540
atgagaactt accctataaa atatccctcc cggtacagtg gacctgtgaa ctaccagcac    3600
cgcttctcca cgttcgagcc cctttccaac aaacccagtg agccctcct ccattcctga     3660 gaaaagagaa aagagtgaaa atacacacac acacacacac acacacacac acacacacac    3720
acacacacac gaggaactgc tttctggact tctg                                3754
```

<210> SEQ ID NO 16
<211> LENGTH: 28
<212> TYPE: DNA
<213> ORGANISM: Rattus sp.

<400> SEQUENCE: 16
gccagagaaa tcaagattat cccatcag                                         28

<210> SEQ ID NO 17
<211> LENGTH: 28

```
<212> TYPE: DNA
<213> ORGANISM: Rattus sp.

<400> SEQUENCE: 17
tcctgcccta acctggcctg caagctgt                                              28

<210> SEQ ID NO 18
<211> LENGTH: 28
<212> TYPE: DNA
<213> ORGANISM: Rattus sp.

<400> SEQUENCE: 18
gccagagaaa tcaagattat cccatcag                                              28

<210> SEQ ID NO 19
<211> LENGTH: 28
<212> TYPE: DNA
<213> ORGANISM: Rattus sp.

<400> SEQUENCE: 19
tcctgcccta acctggcctg caagctgt                                              28

<210> SEQ ID NO 20
<211> LENGTH: 18
<212> TYPE: DNA
<213> ORGANISM: Artificial Sequence
<220> FEATURE:
<223> OTHER INFORMATION: Synthetic

<400> SEQUENCE: 20
actagtgatt gccagaga                                                         18

<210> SEQ ID NO 21
<211> LENGTH: 37
<212> TYPE: DNA
<213> ORGANISM: Artificial Sequence
<220> FEATURE:
<223> OTHER INFORMATION: Synthetic

<400> SEQUENCE: 21
cttatcttat ctaattttat tttcccctgt atgttga                                    37

<210> SEQ ID NO 22
<211> LENGTH: 42
<212> TYPE: DNA
<213> ORGANISM: Artificial Sequence
<220> FEATURE:
<223> OTHER INFORMATION: Synthetic

<400> SEQUENCE: 22
gaaaataaaa ttagataaga taagcattct catctcgtga cg                              42

<210> SEQ ID NO 23
<211> LENGTH: 38
<212> TYPE: DNA
<213> ORGANISM: Artificial Sequence
<220> FEATURE:
<223> OTHER INFORMATION: Synthetic

<400> SEQUENCE: 23
tatcttctat cttatcctaa catctcctct agggggcgt                                  38

<210> SEQ ID NO 24
<211> LENGTH: 36
<212> TYPE: DNA
```

<213> ORGANISM: Artificial Sequence
<220> FEATURE:
<223> OTHER INFORMATION: Synthetic

<400> SEQUENCE: 24
aggataagat agaagatacg ggtggggact cacagc                36

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
ggggttacca gaacactttc aagg                24

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gtcggtatca tcctccacag                20

<210> SEQ ID NO 27
<211> LENGTH: 30
<212> TYPE: DNA
<213> ORGANISM: Artificial Sequence
<220> FEATURE:
<223> OTHER INFORMATION: Synthetic

<400> SEQUENCE: 27
tatcttatcc ttctgacgtc tcactttatg                30

<210> SEQ ID NO 28
<211> LENGTH: 37
<212> TYPE: DNA
<213> ORGANISM: Artificial Sequence
<220> FEATURE:
<223> OTHER INFORMATION: Synthetic

<400> SEQUENCE: 28
cgtcagaagg ataagatagg atgaatgaag gtcttag                37

<210> SEQ ID NO 29
<211> LENGTH: 40
<212> TYPE: DNA
<213> ORGANISM: Artificial Sequence
<220> FEATURE:
<223> OTHER INFORMATION: Synthetic

<400> SEQUENCE: 29
tatcggtatc ttatatctta tcgaccaacc cgtttcctca                40

<210> SEQ ID NO 30
<211> LENGTH: 42
<212> TYPE: DNA
<213> ORGANISM: Artificial Sequence
<220> FEATURE:
<223> OTHER INFORMATION: Synthetic

<400> SEQUENCE: 30
gataagatat aagataccga tacgggagaa ttcacgcagg ag                42

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gccttctggc caatcagcag                                         20

<210> SEQ ID NO 32
<211> LENGTH: 16
<212> TYPE: DNA
<213> ORGANISM: Artificial Sequence
<220> FEATURE:
<223> OTHER INFORMATION: Synthetic

<400> SEQUENCE: 32
gatctgcacc tcagta                                             16

<210> SEQ ID NO 33
<211> LENGTH: 12
<212> TYPE: DNA
<213> ORGANISM: Artificial Sequence
<220> FEATURE:
<223> OTHER INFORMATION: Synthetic

<400> SEQUENCE: 33
tactgaggtg ca                                                 12

<210> SEQ ID NO 34
<211> LENGTH: 24
<212> TYPE: DNA
<213> ORGANISM: Artificial Sequence
<220> FEATURE:
<223> OTHER INFORMATION: Synthetic

<400> SEQUENCE: 34
ttggtcgctc atgagtacct cacc                                    24

<210> SEQ ID NO 35
<211> LENGTH: 26
<212> TYPE: DNA
<213> ORGANISM: Artificial Sequence
<220> FEATURE:
<223> OTHER INFORMATION: Synthetic

<400> SEQUENCE: 35
caaccggtgg tgaggtactc atgagc                                  26

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
gatctaataa gatataataa g                                       21

<210> SEQ ID NO 37
<211> LENGTH: 18
<212> TYPE: DNA
<213> ORGANISM: Artificial Sequence
<220> FEATURE:

<223> OTHER INFORMATION: Synthetic

<400> SEQUENCE: 37
tgcatatctt attatatc                                                        18

<210> SEQ ID NO 38
<211> LENGTH: 16
<212> TYPE: DNA
<213> ORGANISM: Artificial Sequence
<220> FEATURE:
<223> OTHER INFORMATION: Synthetic

<400> SEQUENCE: 38
gatcggctcg ccaatg                                                          16

<210> SEQ ID NO 39
<211> LENGTH: 14
<212> TYPE: DNA
<213> ORGANISM: Artificial Sequence
<220> FEATURE:
<223> OTHER INFORMATION: Synthetic

<400> SEQUENCE: 39
tgcattggcg agcc                                                            14

<210> SEQ ID NO 40
<211> LENGTH: 15
<212> TYPE: DNA
<213> ORGANISM: Artificial Sequence
<220> FEATURE:
<223> OTHER INFORMATION: Synthetic

<400> SEQUENCE: 40
gaaggataag atagg                                                           15

<210> SEQ ID NO 41
<211> LENGTH: 15
<212> TYPE: DNA
<213> ORGANISM: Artificial Sequence
<220> FEATURE:
<223> OTHER INFORMATION: Synthetic

<400> SEQUENCE: 41
atcctatctt atcct                                                           15

<210> SEQ ID NO 42
<211> LENGTH: 15
<212> TYPE: DNA
<213> ORGANISM: Artificial Sequence
<220> FEATURE:
<223> OTHER INFORMATION: Synthetic

<400> SEQUENCE: 42
agcctttcca tgcta                                                           15

<210> SEQ ID NO 43
<211> LENGTH: 15
<212> TYPE: DNA
<213> ORGANISM: Artificial Sequence
<220> FEATURE:
<223> OTHER INFORMATION: Synthetic

<400> SEQUENCE: 43
ttatagcatg gaaag                                                           15

```
<210> SEQ ID NO 44
<211> LENGTH: 15
<212> TYPE: DNA
<213> ORGANISM: Artificial Sequence
<220> FEATURE:
<223> OTHER INFORMATION: Synthetic

<400> SEQUENCE: 44
tgtctcgatg ggtag                                                      15

<210> SEQ ID NO 45
<211> LENGTH: 15
<212> TYPE: DNA
<213> ORGANISM: Artificial Sequence
<220> FEATURE:
<223> OTHER INFORMATION: Synthetic

<400> SEQUENCE: 45
ctcctaccca tcgag                                                      15

<210> SEQ ID NO 46
<211> LENGTH: 12
<212> TYPE: DNA
<213> ORGANISM: Artificial Sequence
<220> FEATURE:
<223> OTHER INFORMATION: Synthetic

<400> SEQUENCE: 46
gatctgataa ga                                                         12

<210> SEQ ID NO 47
<211> LENGTH: 15
<212> TYPE: DNA
<213> ORGANISM: Artificial Sequence
<220> FEATURE:
<223> OTHER INFORMATION: Synthetic

<400> SEQUENCE: 47
tgcatatctt atcag                                                      15

<210> SEQ ID NO 48
<211> LENGTH: 17
<212> TYPE: DNA
<213> ORGANISM: Artificial Sequence
<220> FEATURE:
<223> OTHER INFORMATION: Synthetic

<400> SEQUENCE: 48
atacgccctg gttcctg                                                    17

<210> SEQ ID NO 49
<211> LENGTH: 19
<212> TYPE: DNA
<213> ORGANISM: Artificial Sequence
<220> FEATURE:
<223> OTHER INFORMATION: Synthetic

<400> SEQUENCE: 49
aatgcccata ctgttgagc                                                  19
```